(12) United States Patent
Frey et al.

(10) Patent No.: US 8,500,723 B2
(45) Date of Patent: Aug. 6, 2013

(54) LIQUID FILLED INDEX MATCHING DEVICE FOR OPHTHALMIC LASER PROCEDURES

(75) Inventors: Rudolph W. Frey, Maitland, FL (US); Steven E. Bott, Oviedo, FL (US); Gerrit N. Porter, Winter Springs, FL (US)

(73) Assignee: LensAR, Inc., Orlando, FL (US)

( * ) Notice: Subject to any disclaimer, the term of this patent is extended or adjusted under 35 U.S.C. 154(b) by 785 days.

(21) Appl. No.: 12/509,021

(22) Filed: Jul. 24, 2009

(65) Prior Publication Data

US 2010/0022994 A1    Jan. 28, 2010

Related U.S. Application Data

(60) Provisional application No. 61/083,849, filed on Jul. 25, 2008.

(51) Int. Cl.
*A61B 18/20*    (2006.01)
(52) U.S. Cl.
USPC ............................................. 606/4; 351/245
(58) Field of Classification Search
USPC ........... 606/4, 5, 13, 17; 607/88, 89; 351/216, 351/245; 359/665–667; 372/109, 705
See application file for complete search history.

(56) References Cited

U.S. PATENT DOCUMENTS

| | | | |
|---|---|---|---|
| 3,074,407 A | 1/1963 | Moon et al. | |
| 3,971,382 A | 7/1976 | Krasnov | |
| 3,982,541 A | 9/1976 | L'Esperance, Jr. | |
| 4,024,852 A | 5/1977 | L'Esperance et al. | |
| 4,263,893 A | 4/1981 | Pavlak et al. | |
| 4,309,998 A | 1/1982 | Aron nee Rosa et al. | |
| 4,334,736 A | 6/1982 | Herbert | |
| 4,381,007 A | 4/1983 | Doss | |
| 4,394,144 A | 7/1983 | Aoki | |
| 4,461,294 A | 7/1984 | Baron | |
| 4,477,159 A | 10/1984 | Mizuno et al. | |
| 4,502,816 A | 3/1985 | Creter, Jr. et al. | |
| 4,517,980 A | 5/1985 | Tagnon | |
| 4,537,193 A | 8/1985 | Tanner | |
| 4,538,608 A | 9/1985 | L'Esperance, Jr. | |
| 4,554,917 A | 11/1985 | Tagnon | |

(Continued)

FOREIGN PATENT DOCUMENTS

| | | |
|---|---|---|
| CA | 2553963 A1 | 8/2005 |
| CA | 2680072 A1 | 9/2008 |

(Continued)

OTHER PUBLICATIONS

Akchurin, Garif et al., "Evaluation of the degree of turbidity if cataract lens and its correlation with retinal visual acuity", *SPIE*, vol. 3591, 1999, pp. 74-81.

(Continued)

*Primary Examiner* — Darryl J Collins
(74) *Attorney, Agent, or Firm* — Brinks Hofer Gilson & Lione

(57) ABSTRACT

There is provided a device for use as an interface between a laser surgery device and the eye of a patient. The device is filled with a liquid that matches the index of refraction of the eye. The device further has a curved lens that follows the curvature of the outer surface of the patient's eye. In this manner the interface device, through which the laser beam must travel, has essentially the same index of refraction as the eye.

16 Claims, 2 Drawing Sheets

U.S. PATENT DOCUMENTS

| | | | |
|---|---|---|---|
| 4,561,436 A | 12/1985 | Munnerlyn |
| 4,565,197 A | 1/1986 | Daly |
| 4,573,778 A | 3/1986 | Shapiro |
| 4,576,160 A | 3/1986 | Tanaka |
| 4,579,430 A | 4/1986 | Bille |
| 4,580,559 A | 4/1986 | L'Esperance |
| 4,582,405 A | 4/1986 | Muller et al. |
| 4,583,539 A | 4/1986 | Karlin et al. |
| 4,588,505 A | 5/1986 | Walley et al. |
| 4,601,037 A | 7/1986 | McDonald |
| 4,601,288 A | 7/1986 | Myers |
| 4,607,622 A | 8/1986 | Fritch et al. |
| 4,628,416 A | 12/1986 | Dewey |
| 4,633,866 A | 1/1987 | Peyman et al. |
| 4,638,801 A | 1/1987 | Daly et al. |
| 4,644,948 A | 2/1987 | Lang et al. |
| 4,648,400 A | 3/1987 | Schneider et al. |
| 4,657,013 A | 4/1987 | Hoerenz et al. |
| 4,665,913 A | 5/1987 | L'Esperance, Jr. |
| 4,669,466 A | 6/1987 | L'Esperance, Jr. |
| 4,669,839 A | 6/1987 | Muchel |
| 4,682,595 A | 7/1987 | Hoerenz et al. |
| 4,686,979 A | 8/1987 | Gruen et al. |
| 4,686,992 A | 8/1987 | Dewey et al. |
| 4,702,245 A | 10/1987 | Schroder et al. |
| 4,702,576 A | 10/1987 | Magnante |
| 4,711,540 A | 12/1987 | Yoshino et al. |
| 4,711,541 A | 12/1987 | Yoshino et al. |
| 4,712,543 A | 12/1987 | Baron |
| 4,715,703 A | 12/1987 | Cornsweet et al. |
| 4,718,418 A | 1/1988 | L'Esperance, Jr. |
| 4,719,912 A | 1/1988 | Wienberg |
| 4,721,379 A | 1/1988 | L'Esperance |
| 4,724,522 A | 2/1988 | Belgorod |
| 4,729,372 A | 3/1988 | L'Esperance, Jr. |
| 4,729,373 A | 3/1988 | Peyman |
| 4,732,148 A | 3/1988 | L'Esperance, Jr. |
| 4,732,460 A | 3/1988 | Kele et al. |
| 4,736,744 A | 4/1988 | Koike et al. |
| 4,741,612 A | 5/1988 | Birngruber et al. |
| 4,744,362 A | 5/1988 | Gründler |
| 4,758,081 A | 7/1988 | Barnes |
| 4,765,336 A | 8/1988 | Blaha et al. |
| 4,770,162 A | 9/1988 | L'Esperance et al. |
| 4,770,172 A | 9/1988 | L'Esperance, Jr. |
| 4,770,486 A | 9/1988 | Wang et al. |
| 4,772,116 A | 9/1988 | Schroder et al. |
| 4,773,414 A | 9/1988 | L'Esperance, Jr. |
| 4,775,361 A | 10/1988 | Jacques et al. |
| 4,776,687 A | 10/1988 | Nakanishi et al. |
| 4,798,204 A | 1/1989 | L'Esperance, Jr. |
| 4,820,264 A | 4/1989 | Matsui et al. |
| 4,830,483 A | 5/1989 | Kohayakawa et al. |
| 4,832,043 A | 5/1989 | Ichihashi |
| 4,837,857 A | 6/1989 | Scheller et al. |
| 4,838,266 A | 6/1989 | Koziol et al. |
| 4,840,175 A | 6/1989 | Peyman |
| 4,846,172 A | 7/1989 | Berlin |
| 4,848,340 A | 7/1989 | Bille et al. |
| 4,854,693 A | 8/1989 | Ichihashi et al. |
| 4,856,513 A | 8/1989 | Muller |
| 4,862,888 A | 9/1989 | Yessik |
| 4,863,261 A | 9/1989 | Flammer |
| 4,865,029 A | 9/1989 | Pankratov |
| 4,865,441 A | 9/1989 | Reis |
| 4,866,243 A | 9/1989 | Sakane et al. |
| 4,870,952 A | 10/1989 | Martinez |
| 4,881,808 A | 11/1989 | Bille et al. |
| 4,883,351 A | 11/1989 | Weiss |
| 4,884,884 A | 12/1989 | Reis |
| 4,887,019 A | 12/1989 | Reis et al. |
| 4,887,592 A | 12/1989 | Loertscher |
| 4,891,043 A | 1/1990 | Zeimer et al. |
| 4,900,143 A | 2/1990 | Bessler et al. |
| 4,900,145 A | 2/1990 | Akiyama |
| 4,901,718 A | 2/1990 | Billie et al. |
| 4,902,124 A | 2/1990 | Roy, Sr. et al. |
| 4,903,695 A | 2/1990 | Warner et al. |
| 4,905,711 A | 3/1990 | Bennett et al. |
| 4,907,586 A | 3/1990 | Billie et al. |
| 4,911,160 A | 3/1990 | Thyzel |
| 4,911,711 A | 3/1990 | Telfair et al. |
| 4,917,486 A | 4/1990 | Raven et al. |
| 4,931,053 A | 6/1990 | L'Esperance, Jr. |
| 4,941,093 A | 7/1990 | Marshall et al. |
| 4,951,663 A | 8/1990 | L'Esperance, Jr. |
| 4,953,969 A | 9/1990 | Fedorov |
| 4,966,577 A | 10/1990 | Crosson et al. |
| 4,972,836 A | 11/1990 | Schenck et al. |
| 4,973,330 A | 11/1990 | Azema et al. |
| 4,976,709 A | 12/1990 | Sand |
| 4,988,348 A | 1/1991 | Bille |
| 4,994,058 A | 2/1991 | Raven et al. |
| 5,000,561 A | 3/1991 | Lawniczak et al. |
| 5,000,751 A | 3/1991 | Schroder et al. |
| 5,002,571 A | 3/1991 | O'Donnell, Jr. et al. |
| 5,013,311 A | 5/1991 | Nouri |
| 5,019,074 A | 5/1991 | Muller |
| 5,041,134 A | 8/1991 | O'Donnell |
| 5,048,946 A | 9/1991 | Sklar et al. |
| 5,049,147 A | 9/1991 | Danon |
| 5,054,907 A | 10/1991 | Skylar et al. |
| 5,057,102 A | 10/1991 | Tomioka et al. |
| 5,067,951 A | 11/1991 | Greve |
| 5,090,798 A | 2/1992 | Kohayakawa |
| 5,092,863 A | 3/1992 | Schanzlin |
| 5,094,521 A | 3/1992 | Jolson et al. |
| 5,098,426 A | 3/1992 | Sklar et al. |
| 5,102,409 A | 4/1992 | Balgorod |
| 5,108,388 A | 4/1992 | Trokel |
| 5,108,412 A | 4/1992 | Krumeich et al. |
| 5,112,328 A | 5/1992 | Taboada et al. |
| 5,116,114 A | 5/1992 | Nakamura et al. |
| 5,122,135 A | 6/1992 | Durr et al. |
| 5,123,902 A | 6/1992 | Muller et al. |
| 5,128,509 A | 7/1992 | Black et al. |
| 5,133,708 A | 7/1992 | Smith |
| 5,137,530 A | 8/1992 | Sand |
| 5,141,506 A | 8/1992 | York |
| 5,147,349 A | 9/1992 | Johnson et al. |
| 5,147,352 A | 9/1992 | Azema et al. |
| 5,152,055 A | 10/1992 | L'Esperance, III et al. |
| 5,152,759 A | 10/1992 | Parel et al. |
| 5,163,934 A | 11/1992 | Munnerlyn |
| 5,171,242 A | 12/1992 | Dewey et al. |
| 5,174,021 A | 12/1992 | L'Esperance, III et al. |
| 5,178,635 A | 1/1993 | Gwon et al. |
| 5,188,631 A | 2/1993 | L'Esperance, Jr. |
| 5,194,948 A | 3/1993 | L'Esperance, III et al. |
| 5,196,006 A | 3/1993 | Klopotek et al. |
| 5,196,027 A | 3/1993 | Thompson et al. |
| 5,201,730 A | 4/1993 | Easley et al. |
| 5,202,708 A | 4/1993 | Sasaki et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat et al. |
| 5,226,903 A | 7/1993 | Mizuno |
| 5,246,435 A | 9/1993 | Billie et al. |
| 5,246,436 A | 9/1993 | Rowe |
| 5,257,988 A | 11/1993 | L'Esperance, Jr. |
| 5,258,025 A | 11/1993 | Fedorov et al. |
| 5,263,950 A | 11/1993 | L'Esperance, Jr. |
| 5,263,951 A | 11/1993 | Spears et al. |
| 5,275,593 A | 1/1994 | Easley et al. |
| 5,277,911 A | 1/1994 | Viegas et al. |
| 5,279,298 A | 1/1994 | Flower |
| 5,279,611 A | 1/1994 | McDonnell et al. |
| 5,281,211 A | 1/1994 | Parel et al. |
| 5,282,798 A | 2/1994 | Bruse et al. |
| 5,284,477 A | 2/1994 | Hanna et al. |
| 5,288,293 A | 2/1994 | O'Donnell, Jr. |

| Patent | Date | Inventor |
|---|---|---|
| 5,290,272 A | 3/1994 | Burstein et al. |
| 5,295,989 A | 3/1994 | Nakamura |
| 5,300,020 A | 4/1994 | L'Esperance, Jr. |
| 5,300,061 A | 4/1994 | Easley et al. |
| 5,300,062 A | 4/1994 | Ueno |
| 5,300,063 A | 4/1994 | Tano et al. |
| 5,300,114 A | 4/1994 | Gwon et al. |
| 5,304,168 A | 4/1994 | Sun |
| 5,304,169 A | 4/1994 | Sand |
| 5,311,224 A | 5/1994 | Enomoto |
| 5,312,320 A | 5/1994 | L'Esperance, Jr. |
| 5,312,393 A | 5/1994 | Mastel |
| 5,314,422 A | 5/1994 | Nizzola |
| 5,318,047 A | 6/1994 | Davenport et al. |
| 5,318,560 A | 6/1994 | Blount et al. |
| 5,323,788 A | 6/1994 | Silvestrini et al. |
| 5,324,281 A | 6/1994 | Muller |
| 5,325,134 A | 6/1994 | Kohayakawa |
| 5,334,190 A | 8/1994 | Seiler |
| 5,336,215 A | 8/1994 | Hsueh et al. |
| 5,336,216 A | 8/1994 | Dewey |
| 5,342,351 A | 8/1994 | Blaha et al. |
| 5,342,370 A | 8/1994 | Simon et al. |
| 5,345,948 A | 9/1994 | O'Donnell, Jr. |
| 5,346,491 A | 9/1994 | Oertli |
| 5,347,329 A | 9/1994 | Ota |
| 5,348,551 A | 9/1994 | Spears et al. |
| 5,350,374 A | 9/1994 | Smith |
| 5,354,331 A | 10/1994 | Schachar |
| 5,355,181 A | 10/1994 | Ashizaki et al. |
| 5,356,407 A | 10/1994 | Easley et al. |
| 5,356,409 A | 10/1994 | Nizzola |
| 5,360,424 A | 11/1994 | Klopotek |
| 5,364,388 A | 11/1994 | Koziol |
| 5,364,390 A | 11/1994 | Taboada et al. |
| 5,368,590 A | 11/1994 | Itoh |
| 5,370,641 A | 12/1994 | O'Donnell, Jr. |
| 5,372,595 A | 12/1994 | Gaasterland et al. |
| 5,374,265 A | 12/1994 | Sand |
| 5,376,086 A | 12/1994 | Khoobehi et al. |
| 5,391,165 A | 2/1995 | Fountain et al. |
| 5,395,356 A | 3/1995 | King et al. |
| 5,403,307 A | 4/1995 | Zelman |
| 5,408,484 A | 4/1995 | Weimel |
| 5,411,501 A | 5/1995 | Klopotek |
| 5,412,561 A | 5/1995 | Rosenshein et al. |
| 5,413,555 A | 5/1995 | McMahan |
| 5,423,798 A | 6/1995 | Crow |
| 5,423,800 A | 6/1995 | Ren et al. |
| 5,423,801 A | 6/1995 | Marshall et al. |
| 5,425,727 A | 6/1995 | Koziol |
| 5,425,729 A | 6/1995 | Ishida et al. |
| 5,425,730 A | 6/1995 | Luloh |
| 5,437,657 A | 8/1995 | Epstein |
| 5,437,658 A | 8/1995 | Muller et al. |
| 5,439,462 A | 8/1995 | Bille et al. |
| 5,441,496 A | 8/1995 | Easley et al. |
| 5,441,511 A | 8/1995 | Hanna |
| 5,442,412 A | 8/1995 | Frey et al. |
| 5,442,487 A | 8/1995 | Mizuno |
| 5,445,633 A | 8/1995 | Nakamura et al. |
| 5,460,627 A | 10/1995 | O'Donnell, Jr. |
| 5,461,212 A | 10/1995 | Seiler et al. |
| 5,462,739 A | 10/1995 | Dan et al. |
| 5,465,737 A | 11/1995 | Schachar |
| 5,470,329 A | 11/1995 | Sumiya |
| 5,474,548 A | 12/1995 | Knopp et al. |
| 5,476,511 A | 12/1995 | Gwon et al. |
| 5,480,396 A | 1/1996 | Simon et al. |
| 5,484,432 A | 1/1996 | Sand |
| 5,489,299 A | 2/1996 | Schachar |
| 5,503,165 A | 4/1996 | Schachar |
| 5,507,740 A | 4/1996 | O'Donnell, Jr. |
| 5,514,124 A | 5/1996 | Alpins |
| 5,514,125 A | 5/1996 | Lasser et al. |
| 5,520,679 A | 5/1996 | Lin |
| 5,527,774 A | 6/1996 | Girard |
| 5,529,076 A | 6/1996 | Schachar |
| 5,533,997 A | 7/1996 | Ruiz |
| 5,548,352 A * | 8/1996 | Dewey .................. 351/159.02 |
| 5,549,597 A | 8/1996 | Shimmick et al. |
| 5,556,395 A | 9/1996 | Shimmick et al. |
| 5,573,544 A | 11/1996 | Simon et al. |
| 5,594,753 A | 1/1997 | Frey et al. |
| 5,607,472 A | 3/1997 | Thompson |
| 5,616,139 A | 4/1997 | Okamoto |
| 5,618,284 A | 4/1997 | Sand |
| 5,620,435 A | 4/1997 | Belkin et al. |
| 5,627,162 A | 5/1997 | Gwon et al. |
| 5,632,742 A | 5/1997 | Frey et al. |
| 5,651,782 A | 7/1997 | Simon et al. |
| 5,656,186 A | 8/1997 | Mourou et al. |
| 5,684,560 A | 11/1997 | Roffman et al. |
| 5,699,142 A | 12/1997 | Lee et al. |
| 5,709,868 A | 1/1998 | Perricone |
| 5,722,952 A | 3/1998 | Schachar |
| 5,722,970 A | 3/1998 | Colvard et al. |
| 5,731,909 A | 3/1998 | Schachar |
| 5,738,677 A | 4/1998 | Colvard et al. |
| 5,752,950 A | 5/1998 | Frey et al. |
| 5,773,472 A | 6/1998 | Stjernschantz et al. |
| 5,828,686 A | 10/1998 | Frey et al. |
| 5,843,184 A | 12/1998 | Cionni |
| 5,849,006 A | 12/1998 | Frey et al. |
| 5,886,768 A | 3/1999 | Knopp et al. |
| 5,907,908 A | 6/1999 | Cunanan et al. |
| 5,912,915 A | 6/1999 | Reed et al. |
| 5,919,186 A | 7/1999 | Bath |
| 5,980,513 A | 11/1999 | Frey et al. |
| 5,984,916 A | 11/1999 | Lai |
| 5,993,441 A | 11/1999 | Muller et al. |
| 6,007,578 A | 12/1999 | Schachar |
| 6,013,101 A | 1/2000 | Israel |
| 6,019,472 A * | 2/2000 | Koester et al. .................. 351/219 |
| 6,022,088 A | 2/2000 | Metzler |
| 6,027,494 A | 2/2000 | Frey |
| 6,050,687 A | 4/2000 | Bille et al. |
| 6,055,259 A | 4/2000 | Frey et al. |
| 6,059,772 A | 5/2000 | Hsia et al. |
| 6,070,981 A | 6/2000 | Mihashi et al. |
| 6,099,522 A | 8/2000 | Knopp et al. |
| 6,114,651 A | 9/2000 | Schluter et al. |
| 6,132,424 A | 10/2000 | Tang |
| 6,186,148 B1 | 2/2001 | Okada |
| 6,190,375 B1 | 2/2001 | Frey |
| 6,197,018 B1 | 3/2001 | O'Donnell, Jr. |
| 6,197,056 B1 | 3/2001 | Schachar |
| 6,252,595 B1 | 6/2001 | Birmingham et al. |
| 6,254,595 B1 | 7/2001 | Juhasz et al. |
| 6,261,220 B1 | 7/2001 | Frey et al. |
| 6,271,914 B1 | 8/2001 | Frey et al. |
| 6,271,915 B1 | 8/2001 | Frey et al. |
| 6,275,718 B1 | 8/2001 | Lempert |
| 6,280,435 B1 | 8/2001 | Odrich et al. |
| 6,280,468 B1 | 8/2001 | Schachar |
| 6,299,640 B1 | 10/2001 | Schachar |
| 6,302,877 B1 | 10/2001 | Ruiz |
| 6,302,879 B1 | 10/2001 | Frey et al. |
| 6,312,422 B1 | 11/2001 | Duback |
| 6,312,424 B1 | 11/2001 | Largent |
| 6,313,165 B1 | 11/2001 | Grunberger et al. |
| 6,315,773 B1 | 11/2001 | Frey et al. |
| 6,319,274 B1 | 11/2001 | Shadduck |
| 6,322,545 B1 | 11/2001 | Schachar |
| 6,322,556 B1 | 11/2001 | Gwon et al. |
| 6,324,191 B1 | 11/2001 | Horvath |
| 6,325,791 B1 | 12/2001 | Shimoji |
| 6,325,792 B1 | 12/2001 | Swinger et al. |
| 6,328,732 B1 | 12/2001 | Donitzky et al. |
| 6,344,040 B1 | 2/2002 | Juhasz et al. |
| 6,373,571 B1 | 4/2002 | Juhasz et al. |
| D459,806 S | 7/2002 | Webb |
| D459,807 S | 7/2002 | Webb |
| 6,413,262 B2 | 7/2002 | Saishin et al. |
| D462,442 S | 9/2002 | Webb |
| D462,443 S | 9/2002 | Webb |
| 6,451,008 B1 | 9/2002 | Frey et al. |
| 6,460,997 B1 | 10/2002 | Frey et al. |

| Patent/Publication | Date | Name |
|---|---|---|
| 6,467,906 B1 | 10/2002 | Alpins |
| 6,493,151 B2 | 12/2002 | Schachar |
| 6,494,910 B1 | 12/2002 | Ganem et al. |
| 6,497,483 B2 | 12/2002 | Frey et al. |
| 6,530,917 B1 | 3/2003 | Seiler et al. |
| 6,544,254 B1 | 4/2003 | Bath |
| 6,547,394 B2 | 4/2003 | Doherty |
| 6,554,825 B1 | 4/2003 | Murray et al. |
| 6,585,726 B2 | 7/2003 | Frey et al. |
| 6,588,902 B2 | 7/2003 | Isogai |
| 6,610,686 B1 | 8/2003 | Enrico et al. |
| 6,623,476 B2 | 9/2003 | Juhasz et al. |
| 6,626,445 B2 | 9/2003 | Murphy et al. |
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| 6,648,877 B1 | 11/2003 | Juhasz et al. |
| 6,669,342 B2 | 12/2003 | Liebermann et al. |
| 6,676,653 B2 | 1/2004 | Juhasz et al. |
| 6,693,927 B1 | 2/2004 | Horvath et al. |
| 6,702,853 B1 | 3/2004 | Peyman |
| 6,726,679 B1 | 4/2004 | Dick et al. |
| 6,849,091 B1 | 2/2005 | Cumming |
| 6,863,667 B2 * | 3/2005 | Webb et al. ............ 606/4 |
| 6,905,641 B2 | 6/2005 | Platt et al. |
| 6,923,955 B2 | 8/2005 | Till et al. |
| 6,962,583 B2 | 11/2005 | Kadziauskas et al. |
| 7,044,568 B2 | 5/2006 | Olivera et al. |
| 7,077,838 B2 | 7/2006 | Wong |
| 7,182,759 B2 | 2/2007 | Kadziauskas et al. |
| 7,188,949 B2 | 3/2007 | Bandhauer et al. |
| 7,220,255 B2 | 5/2007 | Lai |
| 7,252,662 B2 | 8/2007 | McArdle et al. |
| 7,264,355 B2 | 9/2007 | Rathjen |
| RE40,002 E | 1/2008 | Lin |
| RE40,184 E | 3/2008 | Lin |
| 7,338,167 B2 | 3/2008 | Zelvin et al. |
| 7,357,504 B2 * | 4/2008 | Fischer et al. ............ 351/200 |
| 7,364,575 B2 | 4/2008 | Van Saarloos |
| 7,390,089 B2 | 6/2008 | Loesel et al. |
| RE40,420 E | 7/2008 | Dick et al. |
| 7,402,159 B2 | 7/2008 | Loesel et al. |
| 7,467,871 B2 | 12/2008 | Lawhorn et al. |
| 7,540,613 B2 | 6/2009 | Severns |
| 7,655,002 B2 | 2/2010 | Myers |
| 7,717,908 B2 | 5/2010 | Ruiz et al. |
| 7,766,903 B2 | 8/2010 | Blumenkranz et al. |
| 7,836,894 B2 | 11/2010 | Brinkmann et al. |
| 7,959,289 B2 | 6/2011 | Cattin-Liebl |
| 8,085,408 B2 | 12/2011 | Everett et al. |
| 8,262,553 B2 | 9/2012 | Weston et al. |
| 8,262,646 B2 | 9/2012 | Frey et al. |
| 2001/0029363 A1 | 10/2001 | Lin |
| 2002/0004658 A1 | 1/2002 | Munnerlyn et al. |
| 2002/0025311 A1 | 2/2002 | Till |
| 2002/0029053 A1 | 3/2002 | Gordon |
| 2002/0049450 A1 | 4/2002 | Myers |
| 2002/0103478 A1 | 8/2002 | Gwon et al. |
| 2002/0110549 A1 | 8/2002 | Till |
| 2002/0138139 A1 | 9/2002 | Till |
| 2002/0140903 A1 | 10/2002 | Schachar |
| 2002/0159028 A1 | 10/2002 | Masaki |
| 2003/0050629 A1 | 3/2003 | Kadziauskas et al. |
| 2003/0055412 A1 | 3/2003 | Lieberman et al. |
| 2003/0076477 A1 | 4/2003 | Matsumoto |
| 2003/0109926 A1 | 6/2003 | Portney |
| 2003/0135272 A1 | 7/2003 | Brady et al. |
| 2003/0139737 A1 | 7/2003 | Lin |
| 2003/0212387 A1 | 11/2003 | Kurtz et al. |
| 2003/0220630 A1 | 11/2003 | Lin et al. |
| 2004/0054359 A1 | 3/2004 | Ruiz et al. |
| 2004/0059321 A1 | 3/2004 | Knopp et al. |
| 2004/0070761 A1 | 4/2004 | Horvath et al. |
| 2004/0143244 A1 | 7/2004 | Gray et al. |
| 2004/0156014 A1 | 8/2004 | Piers et al. |
| 2004/0199149 A1 | 10/2004 | Myers et al. |
| 2004/0199150 A1 | 10/2004 | Lai |
| 2004/0243111 A1 | 12/2004 | Bendett et al. |
| 2004/0249403 A1 | 12/2004 | Loomas et al. |
| 2005/0107773 A1 | 5/2005 | Bergt et al. |
| 2005/0107775 A1 | 5/2005 | Huang et al. |
| 2005/0165387 A1 | 7/2005 | Lubatschowski et al. |
| 2005/0197655 A1 | 9/2005 | Telfair et al. |
| 2005/0203492 A1 | 9/2005 | Nguyen et al. |
| 2005/0243276 A1 | 11/2005 | Van Heugten et al. |
| 2005/0270486 A1 | 12/2005 | Teiwes et al. |
| 2006/0058682 A1 | 3/2006 | Miller et al. |
| 2006/0192921 A1 | 8/2006 | Loesel et al. |
| 2006/0195076 A1 | 8/2006 | Blumenkranz et al. |
| 2006/0215111 A1 | 9/2006 | Mihashi |
| 2006/0259022 A1 | 11/2006 | Lin |
| 2007/0078447 A1 | 4/2007 | Weinacht et al. |
| 2007/0093795 A1 | 4/2007 | Melcher et al. |
| 2007/0093796 A1 | 4/2007 | Raksi et al. |
| 2007/0129693 A1 | 6/2007 | Hunter et al. |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0265603 A1 | 11/2007 | Pinelli |
| 2008/0071254 A1 | 3/2008 | Lummis et al. |
| 2008/0111972 A1 | 5/2008 | Barth et al. |
| 2008/0114386 A1 | 5/2008 | Iliakis et al. |
| 2008/0186551 A1 | 8/2008 | Hanft et al. |
| 2008/0281303 A1 | 11/2008 | Culbertson et al. |
| 2008/0281413 A1 | 11/2008 | Culbertson et al. |
| 2008/0312675 A1 | 12/2008 | Newcott et al. |
| 2009/0069794 A1 | 3/2009 | Kurtz |
| 2009/0088734 A1 | 4/2009 | Mordaunt |
| 2009/0126870 A1 | 5/2009 | Zadoyan et al. |
| 2009/0131921 A1 | 5/2009 | Kurtz |
| 2009/0137988 A1 | 5/2009 | Kurtz |
| 2009/0137991 A1 | 5/2009 | Kurtz |
| 2009/0137993 A1 | 5/2009 | Kurtz |
| 2009/0157063 A1 | 6/2009 | Ruiz et al. |
| 2009/0161065 A1 | 6/2009 | Smith, III et al. |
| 2009/0171327 A1 | 7/2009 | Kurtz et al. |
| 2009/0177189 A1 | 7/2009 | Raksi |
| 2009/0187178 A1 | 7/2009 | Muller et al. |
| 2009/0244482 A1 | 10/2009 | Elsner et al. |
| 2009/0281530 A1 | 11/2009 | Korn |
| 2010/0002837 A1 | 1/2010 | Gertner et al. |
| 2010/0004641 A1 | 1/2010 | Frey et al. |
| 2010/0004643 A1 | 1/2010 | Frey et al. |
| 2010/0022994 A1 | 1/2010 | Frey et al. |
| 2010/0022996 A1 | 1/2010 | Frey et al. |
| 2010/0042079 A1 | 2/2010 | Frey et al. |
| 2010/0060855 A1 | 3/2010 | Graether |
| 2010/0114079 A1 | 5/2010 | Myers et al. |
| 2010/0256614 A1 | 10/2010 | Donitzky et al. |
| 2010/0256615 A1 | 10/2010 | Blumenkranz et al. |
| 2010/0274228 A1 | 10/2010 | Mrochen et al. |
| 2010/0292676 A1 | 11/2010 | Larsen |
| 2010/0292678 A1 | 11/2010 | Frey et al. |
| 2010/0312231 A1 | 12/2010 | Singh |
| 2010/0324542 A1 | 12/2010 | Kurtz |
| 2010/0331829 A1 | 12/2010 | Bor et al. |
| 2011/0022035 A1 | 1/2011 | Porter et al. |
| 2011/0022036 A1 | 1/2011 | Frey et al. |
| 2011/0028950 A1 | 2/2011 | Raksi et al. |
| 2011/0092965 A1 | 4/2011 | Slatkine et al. |
| 2011/0118712 A1 | 5/2011 | Lubatschowski et al. |
| 2011/0137301 A1 | 6/2011 | Bartoli |
| 2011/0149240 A1 | 6/2011 | Alpins |
| 2011/0160710 A1 | 6/2011 | Frey et al. |
| 2011/0160711 A1 | 6/2011 | Naranjo-Tackman et al. |
| 2011/0166557 A1 | 7/2011 | Naranjo-Tackman et al. |
| 2011/0184395 A1 | 7/2011 | Schuele et al. |
| 2011/0187995 A1 | 8/2011 | Frey et al. |
| 2011/0190739 A1 | 8/2011 | Frey et al. |
| 2011/0190740 A1 | 8/2011 | Frey et al. |
| 2011/0292340 A1 | 12/2011 | Shimizu et al. |
| 2012/0016350 A1 | 1/2012 | Myers et al. |
| 2012/0182522 A1 | 7/2012 | Frey et al. |
| 2012/0265181 A1 | 10/2012 | Frey |

| | | | |
|---|---|---|---|
| 2012/0271286 | A1 | 10/2012 | Curatu et al. |
| 2012/0296321 | A1 | 11/2012 | Frey et al. |
| 2012/0330290 | A1 | 12/2012 | Gray et al. |

FOREIGN PATENT DOCUMENTS

| | | |
|---|---|---|
| EP | 0 397 962 A1 | 11/1990 |
| EP | 0 933 060 A1 | 8/1999 |
| EP | 1 970 034 A1 | 9/2008 |
| EP | 1981426 A2 | 10/2008 |
| EP | 1981454 A2 | 10/2008 |
| FR | 2 497 087 A1 | 7/1982 |
| JP | 5-115437 A | 5/1993 |
| WO | WO 91-19539 A1 | 12/1991 |
| WO | WO 01/13838 A1 | 3/2001 |
| WO | WO 03/002010 A1 | 1/2003 |
| WO | WO 2005/070358 A1 | 8/2005 |
| WO | WO 2007/084627 A2 | 7/2007 |
| WO | WO 2007/084694 A2 | 7/2007 |
| WO | WO 2012/051490 A1 | 4/2012 |

OTHER PUBLICATIONS

Al-Ghoul, K. J. et al., "Distribution and Type of Morphological Damage in Human Nuclear Age-Relate Cataracts", *Department of Cell Biology and Anatomy, University of North Carolina and Duke University Eye Center*, 1996, pp. 237-251.

Al-Ghoul, Kristin J. et al., "Structural Evidence of Human Nuclear Fiber Compaction as a Function of Ageing and Cataractogenesis", *Exp. Eye Res.*, vol. 72, 2001, pp. 199-214.

Alio, et al., "Crystalline Lens Optical Dysfunction through Aging", *Ophthalmology*, vol. 112, No. 22, No. 2005, pp. 2022-2029.

Amann, Josef et al., "Increased Endothelial Cell Density in the Paracentral and Peripheral Regions of the Human Cornea", *American Journal of Ophthalmology*, vol. 135, No. 5, 2003, pp. 584-590.

Amendt, M. Strauss et al., "Modeling of bubble dynamics in relation to medical applications", *SPIE*, vol. 2975, 1997, pp. 362-373.

Ansari, Rafat R. et al., "Measuring lens opacity: combining quasi-elastic light scattering with Scheimpflug imaging system", *SPIE*, vol. 3246, 1998, pp. 35-42.

Anschutz, Till, M.D., "Laser Correction of Hyperopia and Presbyopia", vol. 34, No. 4, 1994, pp. 107-137.

Apple, David J. et al., "Preparation and Study of Human Eyes Obtained Postmortem with the Miyake Posterior Photographic Technique", *Ophthalmology*, vol. 97, No. 6, 1990, pp. 810-816.

Armstrong, Larry "A cataract Brakthrough May Be On The Way", *Business Week*, Mar. 23, 1998, pp. 90-92.

Aston, Adam, "Why Settle For 20/20?", *Business Week*, Mar. 17, 2003, at 95.

Azzam, Naiel et al., "Long-term lens organ culture system to determine age-related effects of UV irradiation on the eye lens", Experimental Eye Research, 79, 2004, pp. 903-911.

Back, Arthur P. et al., "Correction of Presbyopia with Contact Lenses: Comparative Success Rates with Three Systems", *Optometry & Vision Science*, vol. 66, No. 8, pp. 518-525.

Balaram, Mini et al., Noncontact Specular Microscopy of Human Lens Epithelium, *IOVS*, vol. 41, No. 2, 2000, pp. 474-481.

Baral, Adiel et al., "Anterior capsulotomy using the $CO_2$ laser", *SPIE*, vol. 3246, 1998, pp. 196-198.

Bath, Patricia E. et al., "Endocapsular Excimer Laser Phakoablation Through a 1-mm Incision", *Opthalmic Laser Therapy*, vol. 2, No. 4, 1987, pp. 245-248.

Beers, A. P. A. et al. "age-Related Changes in the Accommodation Mechanism", *Optometry and Vision Science*, vol. 73, No. 4, pp. 235-242.

Beers, A. P. A. et al., "In Vivo Determination of the Biomechanical Properties of the Component Elements of the Accommodation Mechanism", Vision Res., vol. 34, pp. 2897-2905, 1994.

Bellows, John G., M.D. et al., "B. Cataracta Complicata", 2 pgs.

Ben-Sira, I. et al., "Clinical method for measurement of light back scattering from the in vivo human lens", *Invest. Ophthalmol. Vis. Sci.*, vol. 19, No. 4 (Reports), 1980, pp. 435-437.

Benjamin, William J., "Borish's Clinical Refraction", W.B. Saunders, publishers, copyright 1998, p. 110.

Bettelheim, Frederick A. et al., "Syneretic Response of Aging Normal Human Lens to Pressure", *Investigative Ophthalmology & Visual Science*, vol. 44, No. 1, 2003, pp. 258-263.

Bigler, Emmanuel, "Depth of field and Scheimpflug's rule: a "minimalist" geometrical approach", *ENSMM*, France, 2002, pp. 1-17.

Billie, J. F. et al., "3D Imaging of the Human Eye Using The laser Tomographic Scanner Lts", *Institue of Applied Sciences, University of Heidelburg*, undated, 2 pgs.

Bito, L.Z. et al., "Age-dependent loss of accommodative amplitude in rhesus monkeys: an animal model for presbyopia", *Invest. Ophthalmol. Vis. Sci.*, vol. 23, No. 1, 1982, pp. 23-31.

Bor, Zs. PhD., et al., "Plume Emission, Shock Wave and Surface Wave Formation During Excimer Laser Ablation of the Cornea", *Supplement to Retroactive & Corneal Surgery*, vol. 9, Mar./Apr. 1993, pp. S110-S115.

Borja, David et al., "Crystalline Lens MTF Measurement During Simulated Accommodation", *SPIE*, vol. 5688, 2005, pp. 26-32.

Borkman, Raymond F. "Evidence for a Free Radical Mechanhism in Aging and u.v.-Irradiated Ocular Lenses", *Exp. Eye Res.* (1977) 25, 303-309.

Braham, Lewis, "Eye Surgery: It's Getting Sharper", *Business Week*, Oct. 18, 2004, at 142.

Breitenfeld, P. et al., "Finite Element Method-Simulation of the Human Lens During Accommodation", *Proc. SPIE Therapeutic Laser Applications and Laser-Tissue Interactions II*, vol. 5863, 2005, 9 pgs.

Breitling, Detlef et al., "Fundamental aspects in machining of metals with short and ultrashort laser pulses", *SPIE*, vol. 5339, pp. 1-15.

Bron, A.J., "The Ageing Lens", *Opthalmologics*, vol. 214, pp. 86-104.

Brown, Nicholas, "Dating the onset of cataract", *Transactions of the Opthalmological Society of the United Kingdom*, vol. 96, 1976, pp. 18-23.

Brown, Niocholas "The Change in Lens Curvature with Age", *Exp. Eye Res.* (1974), vol. 19, pp. 175-183.

Brown, Nicholas "The Change in Shape and Internal Form of the Lens of the Eye on Accommodation", *Exp. Eye Res.* (1973) vol. 15, pp. 441-459.

Burd, H.J. et al., "Can reliable values of Young's modulus be deduced from Fisher's (1971) spinning lens measurements?", *Vision Research*, 2005, pp. 1-15.

Burd, H.J. et al., "Numerical modeling of the accommodating lens", *Vision Research*, vol. 42, 2002, pp. 2235-2251.

Campbell, Melanie C. W., "Measurement of Refractive Index In an Intact Crystalline Lens", *Vision Res.*, vol. 24, No. 5, 1984, pp. 409-415.

Carey, James et al., "Propagation and Characterization of Ultrashort Laser Pulses", *Spectroscopy of Systems with Spatially Confined Structures*, Ed. Rino Di Bartolo, Kluwer Academic Press, Netherlands, 2003, pp. 1-30.

Charles, M. W. et al., "Dimensions of the Human Eye Relevant to Radiation Protection", *Phys. Med. Biol.*, 1975, vol. 20, No. 2, © 1975, pp. 2002-2218.

Chen, Wei-Li et al., Ultrasound Biomicroscopic Findings in Rabbit Eyes Undergoing Scleral Suction during Lamellar Refractive Surgery, *IOVS*, vol. 43, No. 12, 2002, pp. 3665-3672.

Claflin, E. S. et al., "Configuring an electrostatic membrane mirror by least-squares fitting with analytically derived influence functions", *J. Opt. Soc. Am. A.*, vol. 3, No. 11, 1986, pp. 1833-1839.

Coleman, D. Jackson et al., "Presbyopia, Accommodation, and the Mature Catenary", *Ophthalmology*, vol. 108, No. 9, 2001, pp. 1544-1551.

Cook, Christopher A. et al., "Aging of the Human Crystalline Lens and Anterior Segment", *Vision Res.*, vol. 34, No. 22, pp. 2945-2954.

Costagliola, Ciro et al., "ArF 193 nm Excimer Laser Corneal Surgery as a Possible Risk Factor in Cataractogenesis", *Exp. Eye Res.* (1994), vol. 58, pp. 453-457.

Cotlier, Edward, M.D., "The Lens", *Adler's Physiology of the Eye*, pp. 268-290.

Crawford, Kathryn S. et al., "The Role of the Iris in Accommodation of Rhesus Monkeys", *Investigative Ophthalmology & Visual Science*, vol. 31, No. 10, 1990, pp. 2185-2190.

Croft, Mary Ann et al., Accommodative Ciliary Body and Lens Function in Rhesus Monkeys, I: Normal Lens, Zonule and Ciliary Process Configuration in the Iridectomized Eye, *IOVS*, vol. 47, No. 3, 2006, pp. 1076-1086.

Croft, Mary Ann et al., "Accommodation and Presbyopia", *Int Ophthalmol Clin*, vol. 41, pp. 33-46.

Croft, Mary Ann et al., "The Zonula, Lens, and Circumlental Space in the Normal Iridectomized Rhesus Monkey Eye", *IOVS*, vol. 47, No. 3, 2006, pp. 1087-1095.

Croft, Mary Ann et al., "Accommodation and Presbyopia: The Ciliary Neuromuscular View", *Opthalmol Clin N Am*, vol. 19, 2006, pp. 13-24, ophthalmology.theclinics.com.

Cromie, William J., "Laser Makes History's Fastest Holes", *The Harvard University Gazette*, http://www.news.harvard.edu/gazette/1999/10.07/laser.html.

Czygan, G. et al., "Mechanical testing of isolated senile human eye lens nuclei", *Med. Eng. Phys.*, vol. 18, No. 5, 1996, pp. 345-349.

Datta, Debajyoti, "Tissue Surgery and Subcellular Photodisruption with Femtosecond Laser Pulses", *Thesis for Dept. of Physics*, Harvard University, 2002, pp. 1-74.

Dausinger, Friedrich et al., "Micro-machining with ultrashort laser pulses: From basic understanding to technical applications", *SPIE*, No. 5147, 2002, pp. 1-10.

Dholakia, Sheena A. et al., "Prospective evaluation of phacoemulsification in adults younger than 50 years", *J Cataract Refract Surg*, vol. 31, 2005, pp. 1327-1333.

Douven, Lucien F.A. et al., "Characterization of Mechanical Behaviour of Human Skin In Vivo", *SPIE*, vol. 3914, 2000, pp. 618-629.

Ehrmann, Klaus et al., "Evaluation of porcine crystalline lenses in comparison with molded polymer gel lenses with an improved ex vivo accommodation simulator", *SPIE*, vol. 5688, 2005, pp. 240-251.

Ehrmann, Klaus et al., "Ex Vivo Accommodation Simulator II—Concept and Preliminary Results", *SPIE*, vol. 5314, 2004, pp. 48-58.

El-Osta, Austen A.R. et al., "In vitro model for the study of human posterior capsule opacification", *J Cataract Refract Surg*, vol. 29, 2003, pp. 1593-1600.

Erpelding, Todd N. et al., "Bubble-Based Acoustic Radiation Force for Monitoring Intraocular Lens Elasticity", *IEEE Ultrasonics Symposium*, 2004, pp. 732-735.

Fagerholm, Per P.P., "The Response of the Lens to Trauma", *Trans. Ophtal. Soc. U. K.* (1982) vol. 102, p. 375.

Farxsworth, P.N. et al., "Anterior Zonular Shifts with Age", *Exp. Eye Res.* (1979), vol. 28, pp. 291-297.

Findl, Oliver et al., "Laserinterferometric Assessment of Pilocarpine-Induced Movement of an Accommodating Intraocular Lens—A Randomized Trial", *Ophthalmology*, vol. 111, No. 8, 2004, pp. 1515-1521.

Fisher, R.F. et al., "Changes in lens fibres after damage to the lens capsule", *Lens Clinic*, St. May's Hospital, London, undated, 4 pgs.

Fisher, R.F., "Presbyopia and the Changes With Age in the Human Crystalline Lens", *J. Physiol.*, vol. 228, 1973, pp. 765-779.

Fisher, R. F., "The Ciliary Body in Accommodation", *Trans. Opthalmol. Soc. U.K.* (1986), vol. 105, p. 208.

Fisher, R.F., "The Force of Contraction of the Human Ciliary Muscle During Accommodation", *J. Physiol.*, vol. 270, 1977, pp. 51-74.

Fisher, R. F. et al., "The elastic constants and ultrastructural organization of a basement membrane (lens capsule)", *Proc. R. Soc. Lond. B.* 193, 1976, pp. 335-358.

Fisher, R.F., "The Elastic Constants of The Human Lens", *J. Physiol.* (1971), vol. 212, pp. 147-180.

Fisher, R.F., "Elastic Constants of The Human Lens Capsule", *J. Physiol.* (1969), vol. 201, pp. 1-19.

Fisher, R. F., "The Mechanics of Accommodation in Relation to Presbyopia", *Eye*, (1988), vol. 2, pp. 646-649.

Fleck, Brian W. et al., "Q-switched Nd:YAG laser disruption of rabbit lens nucleus", *Laser and Light in Ophthalmology*, 1990, vol. 3. No. 3, pp. 227-232.

Foster, C. Stephen et al., "Smolin and Thoft's The Cornea: Scientific Foundations and Clinical Practice", *The New England Journal of Medicine*, 353:23, 2005, 2 pgs.

Fujimoto, James et al., "Biomedical Optics", Photonics West, *SPIE*, vol. 5686, 2005, pp. 23-70.

Garner, Margaret H. et al., "Selective oxidation of cysteine and methionine in normal and senile cataractous lenses", *Proc. Natl. Acad. Sci. USA*, vol. 77, No. 3, Mar. 1980, pp. 1274-1277.

Gayen, Tapan K. et al., "Near-infrared laser welding of aortic and skin tissues and microscopic investigation of welding efficacy", *SPIE*, vol. 4949, 2003, pp. 182-185.

Gershenzon, A. et al., "Clinical and Epidemiology—New software for lens retro-illumination digital image analysis", *Australian and New Zealand Journal of Ophthalmology*, 1999, vol. 27, pp. 170-172.

Giblin, Frank J. et al., "Nuclear Light Scattering, Disulfide Formation and Membrane Damage in Lenses of Older Guinea Pigs Treated with Hyperbaric Oxygen", *Exp. Eye Res.* (1995), vol. 60, pp. 219-235.

Gimbel, Howard V. et al., "Intrastromal Photorefractive Keratectomy with the Nd:YLF Laser", Gimbel and Beldays, pp. 139-145.

Glasser, Adrian et al., "Accommodative Changes in Lens Diameter in Rhesus Monkeys", *IOVS*, vol. 47, No. 1, 2006, pp. 278-286.

Glasser, Adrian et al., "On modeling the causes of presbyopia", *Vision Research*, 2001, vol. 41, pp. 3083-3087.

Glasser, Adrian et al., "Presbyopia and the Optical Changes in the Human Crystalline Lens with Age", *Vision Res.*, 1998, vol. 38, No. 2, pp. 209-229.

Glasser, Adrian et al., "Ultrasound Biomicroscopy of the Aging Rhesus Monkey Ciliary Region", *Optometry and Vision Science*, 2001, vol. 78, No. 6, pp. 417-424.

Goodenough, Daniel A., "Lens gap junctions: a structural hypothesis for nonregulated low-resistance intercellular pathways", *Invest. Ophthalmol. Visual Sci.*, vol. 18, No. 11, Nov. 1979, pp. 1104-1122.

Grace, Jeffery M. et al., "Repetitively Pulsed Ruby Lasers As Light Sources For High-Speed Photography", *Optical Engineering*, vol. 37, No. 8, 1998, pp. 1-26.

Gwon, Arlene et al., "Focal laser photophacoablation of normal and cataractous lenses in rabbits: Preliminary report", *J. Cataract Refract Surg*, vol. 21, 1995, pp. 282-286.

Habib, Maged S. et al., "Myopic Intrastromal Photorefractive Keratectomy With the Neodymium-Yttrium Lithium Fluoride Picosecond Laser in the Cat Cornea", *Arch Ophthalmol.*, 1995; 113:499-505.

Hahn, D.W., "Dynamics of Ablation Plume Particles Generated During Excimer Laser Corneal Ablation", *Laser in Surgery and Medicine*, vol. 16, 1995, pp. 384-389.

Hamaoui, Marie et al., "Ex-vivo testing of crystalline lens substitutes: a pilot study", *SPIE*, vol. 3908, 2000, pp. 123-130.

Hammer, Daniel X. et al., "Dual OCT/SLO Imager with Three-Dimensinal Tracker", *SPIE*, vol. 5688, 2005, pp. 33-44.

Hara, Tsutomu, M.D. et al., "Complications associated with endocapsular balloon implantation rabbit eyes", *J Cataract Refract Surg*, vol. 20, Sep. 1994.

Harding, J. J., "Disulphide Cross-linked Protein of High Molecular Weight in Human Cataractous Lens", *Exp. Eye Res.* (1973), 17, pp. 377-383.

Hartwick, Andrew T. E. et al., "Ephitelial activity of hexokrinase and glucose-6-phosphate dehydrogenase in cultured bovine lenses recovering from pharmaceutical-induced optical damage", *Molecular Vision*, vol. 9, 2003, pp. 594-600.

Heisterkamp, Alexander et al., "Nonlinear effects inside corneal tissue after fs-photodisruption", *SPIE*, vol. 4433, 2001, pp. 55-60.

Heisterkamp, Alexander et al., "Pulse energy dependence of subcellular dissection by femtosecond laser pulses", *Optics Express*, vol. 13, No. 10, 2005, pp. 3690-3696.

Hemenger, Richard P. et al., "Change With Age of the Refractive Index Gradient of the Human Ocular LEns", *Investigative Ophthalmology & Visual Science*, Mar. 1995, vol. 36, No. 3, pp. 703-707.

Heys, Karl Robert et al., "Massive increase in the stiffness of the human lens nucleus with age: the basis for presbyopia?", *Molecular Vision*, vol. 10, 2004, pp. 956-963.

Ho, A. et al., "Feasibility pf simultaneous correction of ametropia by varying gel refractive index with phaco-ersatz", *SPIE*, vol. 4245, 2001, pp. 119-128.

Hoffman, Richard S. et al., "Refractive lens exchange as a refractive surgery modality", Copyright © *Lippincott Williams & Wilkins*, pp. 22-28.

Holzer, Mike P. et al., "Corneal flap complications in refractive surgery—Part 1: Development of an experimental animal model", *J Cataract Refract Surg*, vol. 29, 2003, pp. 795-802.
Holzer, Mike P. et al., "Corneal flap complications in refractive surgery—Part 2: Postoperative treatments of diffuse lamellar keratitis in an experimental animal model", *J Cataract Refract Surg*, vol. 29, 2003, pp. 803-807.
Horwitz, Joseph, "α-Crystallin can function as a molecular chaperone", *Proc. Natl. Acad. Sci. USA*, 89 (1992).
Hu, Tian-Sheng et al., "Reversal of Galactose Cataract with Sorbinil in Rats", *Investigative Ophthalmology & Visual Science*, May 1983, vol. 24, pp. 640-644.
Huber, G. et al., "Room-temperature 2-pm HO:YAG and 3-pm ER:YAG Lasers", *Journal de Physique*, undated. 3 pgs.
Hunter, David, "First, Gather the Data", *New England Journal of Medicine*, 354:4, 2006, pp. 329-331.
Jacques, Paul F. et al., "Long-term vitamin C supplement use and prevalence of early age-related lens opacities", *Am J Clin Nutr*, 1997; 66, pp. 911-916.
Johannesson, Mattias, "Active Range Imaging 2", PhD-Thesis: SIMD architectures for Range and Radar Imaging, *Linkoping Studies in Science and Technology*, Dissertations No. 399, 2005 pp. 1-34.
Jones, C.E. et al., "Refractive index distribution and optical properties of the isolated human lens measured using magnetic resonance imaging (MRI)", *Vision Research*, vol. 45, 2005, pp. 2352-2366.
Juhasz, T. et al., "Time-resolved Studies of Plasma-Mediated Surface Ablation of Soft Biological Tissue with Near-Infrared Picosecond Laser Pulses", *SPIE*, vol. 2975, 1997, pp. 271-281.
Juhasz, Tibor, Ph.D. et al., "Dynamics of Shock Waves and Cavitation Bubbles Generated by Picosecond Laser Pulses in Corneal Tissue and Water", *Lasers in Surgery and Medicine*, 15, 1994, pp. 91-98.
Kasthurirangan, Sanjeev, "Amplitude dependent accommodative dynamics in humans", *Vision Research*, vol. 43, 2003, pp. 2945-2956.
Kasthurirangan, Sanjeev, "Influence of Amplitude and Starting Point on Accommodative Dynamics in Humans", *IOVS*, vol. 46, No. 9, 2005, pp. 3463-3472.
Kaufman, Paul L., M.D., "Accommodation and Presbyopia: Neuromuscular and Biophysical Aspects", *Adler's Physiology of the Eye*, pp. 391-411.
Keeney, Arthur H., M.D., "Intralenticular Foreign Bodies", *Arch Ophthal.*, vol. 86, Nov. 1971, pp. 499-501.
König, Karsten et al., "Are Femtosecond Lasers Safe for Ophthalmic Applications?", *Fraunhofer Institute of Biomedical Technologies*, undated, pp. 1-16.
König, Karsten et al., "First in vivo animal studies on intraocular nanosurgery and multiphoton tomography with low-energy 80 MHz near infrared femtosecond laser pulses", *SPIE*, vol. 5314, 2004, pp. 262-269.
König, Karsten et al., "Cornea surgery with nanojoule femtosecond laser pulses", *SPIE*, vol. 5688, 2005, pp. 288-293.
Koopmans, Steven A. et al., "Polymer Refilling of Presbyopic Human Lenses In Vitro Restores the Ability to Undergo Accommodative Changes", *IOVS*, vol. 44, No. 1, 2003, pp. 250-257.
Koretz, Jane F. et al., "A Model for Accommodation in the Young Human Eye: The Effects of Lens Elastic Anisotropy on the Mechanism", *Vision Res.*, vol. 23, No. 12, 1983, pp. 1679-1686.
Koretz, Jane F. et al., "Accommodation and Presbyopia in the Human Eye—Aging of the Anterior Segment", *Vision Res.*, vol. 29, No. 12, 1989, pp. 1685-1692.
Koretz, Jane F. et al., "Accommodation and Presbyopia in the Human Eye—Changes in the Anterior Segment and Crystalline Lens With Focus", *IOVS*, vol. 38, No. 3, 1997, pp. 569-578.
Koretz, Jane F. et al., "Analysis of Human Crystalline Lens Curvature as a Function of Accommodative State and Age", *Vision Res.*, vol. 24, No. 10, 1984, pp. 1141-1151.
Koretz, Jane F. et al., "How the Human Eye Focuses", *Scientific American*, Jul. 1988, pp. 92-99.
Koretz, Jane F. et al., "Model of the Accommodative Mechanism in The Human Eye", *Vis. Res.*, vol. 22, 1982, pp. 917-927.
Koretz, Jane F. et al., "Scheimpflug and high-resolution magnetic resonance imaging of the anterior segment: a comparative study", *J. Opt. Soc. am. A*, vol. 21, No. 3, 2004, pp. 346-354.
Koretz, Jane F. et al., "The Zones of Discontinuity in the Human Lens: Development and Distribution with Age", *Vision Res.*, vol. 34, No. 22, 1994, pp. 2955-2962.
Krag, Susanne et al., "Biomechanical Characteristics of the Human Anterior Lens Capsule in Relation to Age", *Investigative Ophthalmology & Visual Science*, Feb. 1997, vol. 58, No. 2, pp. 357-362.
Krag, Susanne, "Biomechanical measurements of the lens capsule", *Scandinavian University Theses*, 1999, 3 pgs.
Krag, Susanne et al., "Mechanical Properties of the Human Posterior Lens Capsule", *IOVS*, vol. 44, No. 2, 2003, pp. 691-696.
Krauss, Joel et al., "Laser Interactions With the Cornea", *Survey of Ophthalmology* A492, vol. 31, No. 1, 1986, pp. 37-53.
Kronemyer, Bob, "Accommodating IOL? Impossible, Recent Study Seems to Say". *Ocular Surgery News*, http://www.slackmc.com, Sep. 15, 1996.
Krueger, Ronald R. et al., "Experimental Increase in Accommodative Potential after Neodymium: Yttrium-Aluminum-Garnet Laser Photodisruption of Paired Cadaver Lenses", *Ophthalmology*, vol. 108, No. 11, 2001, pp. 2122-2129.
Krueger, Ronald R. et al., "First safety study of femtosecond laser photodisruption in animal lenses: Tissue morphology and cataractogenesis", *J Cataract Refract Surg*, vol. 31, 2005, pp. 2386-2394.
Krueger, Ronald R., M.D. et al., "Ultrastructure of Picosecond Laser Intrastromal Photodisruption", *Journal of Refractive Surgery*, vol. 12, Jul./Aug. 1996, pp. 607-612.
Krueger, Ronald R., M.D., et al., "Nonmechanical Microkeratomes Using Laser and Water Jet Technology", 33 pgs.
Kurapkienė, S. et al., "The relationship of ultrasonic and mechanical properties of human nuclear cataract. A pilot study", *Ultragarsas*, vol. 54, No. 1, 2005, pp. 1392-2114.
Kuizenga, Dirk J., "FM-Laser Operatiob of the Nd:YAG Laser", *IEEE Journal of Quantum Electronics*, Bol. 6, No. 11, 1970, pp. 673-677.
Kurtz, Ron et al., "Femtosecond Laser Corneal Refractive Surgery", *SPIE*, vol. 3591, 1999, pp. 209-219.
Kurtz, Ron et al., "Ophthalmic Applications of Femtosecond Lasers", *SPIE*, vol. 3616, 1999, pp. 51-65.
Kurtz, Ron M. et al., "Optimal Laser Parameters for Intrastromal Corneal Surgery", *SPIE*, vol. 3255, 1998, pp. 56-66.
Kurtz, Ron M., MD, et al., "Photo-disruption in the Human Cornea as a Function of Laser Pulse Width", *Journal of Refractive Surgery*, vol. 13, Nov./Dec. 1997, pp. 653-658.
Kuszak, J. R. et al., "A Quantitative Analysis of Sutural Contributions to Variability in Back Vertex Distance and Transmittance in Rabbit Lenses as a Function of Development, Growth, and Age", *Optometry and Vision Science*, vol. 79, No. 3, 2002, pp. 193-204.
Kuszak, J. R. et al., "Biochemistry of The Crystalline Lens; Anatomy of Aged and Senile Cataractous Lenses", pp. 564-575.
Kuszak, J. R. et al., "Development of lens sutures", *Int. J. Dev. Biol.*, vol. 48, 2004, pp. 889-902.
Kuszak, J. R. et al., "Electron Microscope Observations of the Crystalline Lens", *Microscopy Research and Technique*, 1996, vol. 33, pp. 441-479.
Kuszak, J. R. et al., "Fibre cell organization in crystalline lenses", *Experimental Eye Research*, vol. 78, 2004, pp. 673-687.
Kuszak, J. et al., "Gap Junctions of Chick Lens Fiber Cells", *Exp. Eye Res.* 27, (1978), pp. 495-498.
Kuszak, J. R. et al., "Quantitative Analysis of Animal Model Lens Anatomy: Accommodative Range is Related to Fiber Structure and Organization", *Dept. of Ophthalmology and Pathology*, undated, 26 pgs.
Kuszak, J. R. et al., "Lens Optical Quality and Lens Sutures", *Investigative Ophthalmology & Visual Science*, vol. 32, No. 7, Jun. 1991, pp. 2123-2129.
Kuszak, J. R. et al., "Lens Optical Quality is a Direct Function of Lens Sutural Architecture", *Investigative Ophthalmology & Visual Science*, vol. 32, No. 7, Jun. 1991, pp. 2119-2122.
Kuszak, J. R. et al., "Suppression of Post-Vitrectomy Lens Changes in the Rabbit by Novel Benzopyranyl Esters and Amides", *Exp. Eye Res.*, vol. 75, 2002, pp. 459-473.

Kuszak, J. R. et al., "The Relationship Between Rabbit Lens Optical Quality and Sutural Anatomy after Vitrectomy", *Exp. Eye Res.*, vol. 71, 2000, pp. 267-281.

Kuszak Jer R. et al., "The Structure of the Vertebrate Lens", Chapter 4, pp. 71-118.

Kuszak, J. et al., "The Surface Morphology of Embryonic and Adult Chick Lens-Fiber Cells", *The American Journal of Anatomy*, pp. 395-410.

Kuszak, J. R. et al., "The Use of an Ex Vivo Mechanical Stretching Apparatus to Examine Fiber Ultrastructure During Accommodation", Dept. of Ophthalmology, Illinois College of Optometry, undated, 1 pg.

Kuwabara, Toichiro, et al., "Electron Microscopic Study of Galactose-Induced Cataract", *Investigative Ophthalmology*, vol. 8, No. 2, Apr. 1969, pp. 133-149.

L'Esperance, Jr. "*Ophthalmic Lasers Photocoagulation, Photoradiation and Surgery*", 2$^{nd}$ Edition, copyright 1983, The C.V. Mosby Company, pp. 529-538.

Lerman, Sidney, et al., "A Method for Detecting 8-Methoxypsoralen in the Ocular Lens", *Science*, vol. 197, Sep. 23, 1977, 1287-1288.

Lerman, Sidney, et al., "Spectroscopic Evaluation and Classification of the Normal, Aging, and Cataractous Lens", *Ophthl. Res.*, 8: (1976), pp. 335-353.

Lerman, Sidney, et al., "Photosensitization of the lens by 8-methoxypsoralen", *Invent. Ophthalmol. Visual Sci.*, vol. 16, No. 11, Nov. 1977, pp. 1066-1068.

Lerman, Sidney, et al., "Psoralen-long-wave Ultraviolet Therapy and Human Cataractogenesis", *Invent. Ophthalmol. Visual Sci.*, vol. 23, No. 6, Dec. 1982, pp. 801-804.

Lerman, Sidney, M.D., "Photosensitizing Drugs and Their Possible Role in Enhancing Ocular Toxicity", *Ophthalmology*, Mar. 1986, vol. 93, No. 3, pp. 304-318.

Lim, Seung Jeong, M.D. et al., "Analysis of zonular-free zone and lens size in relation to axial length of eye with age", *J Cataract Refract Surg*, vol. 24, Mar. 1998, pp. 390-396.

Liu, Xinbing et al., "In vivo plasma-mediated ablation as a function of laser pulse width", *SPIE*, vol. 2975, 1997, pp. 282-288.

Loerscher, Hanspeter et al., "Noncontact Trephination of the Cornea Using a Pulsed Hydrogen Floride Laser", *American Journal of Ophthalmology*, vol. 104, pp. 471-475.

Loesel, Frieder H. et al., "Laser-Induced Optical Breakdown on Hard and Soft Tissues and Its Dependence on the Pulse Duration: Experiment and Model", *IEEE Journal of Quantum Electronics*, vol. 32, No. 10, 1996, pp. 1717-1722.

Lou, Marjorie F., et al., "Protein-Thiol Mixed Disulfides in Human Lens", *Academic Press Limited*, 1992, pp. 889-896.

Lutze, Margaret et al., "Lenses of Diabetic Patients "Yellow" at an Accelerated Rate Similar to Older Normals", *Investigative Ophthalmology & Visual Science*, vol. 32, No. 1, Jan. 1991, pp. 194-199.

Maguen, Ezra, et al., "Excimer Laser Ablation of the Human Lens at 308 nm with a Fiber Delivery System", *J. Cataract Refract Surg.*, vol. 15, Jul. 1989, pp. 409-414.

Manns, Fabrice et al., "Radius of Curvature and Asperacity of the Anterior and Posterior Surface of Human Cadaver Crystalline Lenses", *Science Direct Experimental Eye Research*, 78, 2004, pp. 39-51.

Marion, II, John E. et al., "Medical Applications of Ultra-Short Pulse Lasers", SPIE, vol. 3616, 1999, pp. 42-50.

Masters, B.R., "Three-dimensional Microscopic Tomographic Imaging of the Cataract in a Human Lens In Vivo", *Optics Express 332*, vol. 3, No. 9, 1998, pp. 332-338.

Mathias, R.T. et al., "Physiological Properties of the Normal Lens", *Physiological Review*, vol. 77, No. 1, 1997, pp. 21-50.

McDonald, Marguerita B., et al., "Central Photorefractive Keratectomy for Myopia", *Arch Ophthalmol*, vol. 108, Jun. 1990, pp. 799-808.

Michael, Ralph et al., "Refractive Index of Lens Fiber Membranes in Different Parts of the Crystalline Lens", *Proceedings of SPIE*, vol. 4611, 2002, pp. 159-164.

Moffat, B.A. et al., "Age-Related Changes in Refractive Index Distribution and Power of the Human Lens as Measured by Magnetic Resonance Micro-Imaging In Vitro", *Vision Research*, vol. 42, 2002, pp. 1683-1693.

Mutri, Donald O., et al., "A Video Technique for Phakometry of the Human Crystalline Lens", *Investigative Ophthalmology, & Visual Science*, vol. 33, No. 5, Apr. 1992, pp. 1771-1781.

Myers, Raymond I., "Novel Approaches to Correction of Presbyopia With Laser Modification of the Crystalline Lens", *Journal of Refractive Surgery*, vol. 14, 1998; pp. 136-139.

Myers, O.D., Raymond I. et al., "Feasibility of Using Lasers to Retard Cataract Development in the Ocular Lens by Restoring Lens Movement"; undated, pp. 1-22.

Nanevicz, Tania M., et al., "Excimer Laser Ablation of the Lens", *Arch Ophthamol*, vol. 104, Dec. 1986, pp. 1825-1829.

Neev, Joseph, "Ultrashort Pulse Lasers: A New Tool for Biomedical Applications", *SPIE*, vol. 3255; pp. 2-7.

Oberheide, Uwe et al., "Therapy Monitoring of Laser Cyclophotocoagulation", *Proceedings of SPIE*, vol. 4611, 2002, pp. 48-53.

O'Donnell, Colleen B., et al., "Ablation Smoothness as a Function of Excimer Laser Delivery System", *J. Cataract Refract Surg.*, vol. 22, Jul./Aug. 1996, pp. 682-685.

O'Donnell, Colleen B., et al., "Surface Roughness in PMMA is Linearly Related to the Amount of Excimer Laser Ablation", *Journal of Refractive Surgery*, vol. 12, Jan./Feb. 1996, pp. 171-174.

Oriowo, Olanrewaju Matthew, "A Study of Ultraviolet Radiation Effects on Procine Crystalline Lens and Development of a New Assay Methodology for UV Cataractogenesis Investigation", *A Thesis Presented to the University of Waterloo*, 2000, pp. i-xix and 1-218.

Ostrin, Lisa A. et al., "Effects of Pirenzepine on Pupil Size and Accommodation in Rhesus Monkeys", *Investigative Ophthalmology & Visual Science*, Oct. 2004, vol. 45, No. 10, pp. 3620-3628.

Ostrin, Lisa A. et al., "The Effects of Phenylephrine on Pupil Diameter and Accommodation in Rhesus Monkeys"; *Investigative Ophthalmology & Visual Science*, 2004, vol. 45, No. 1, pp. 215-221.

Ostrin, Lisa A. et al., "Comparisons Between Pharmacologically and Edinger-Westphal-Stimulated Accommodation in Rhesus Monkeys", *Investigative Ophthalmology & Visual Science*, 2005, vol. 46, No. 2, pp. 609-617.

Parel, Jean-Marie et al., "Intraocular Implants for the Surgical Correction of Presbyopia"; *Ophthalmic Technologies X*, Proceedings of SPIE, vol. 3908, 2000, pp. 115-122.

Patel, C.K. et al., "The Ageing Lens", *Association of Optometrists, City University*, London; undated, www.optometry.co.uk; pp. 27-31.

Pau, Hans et al., "The increasing sclerosis of the human lens with age and its relevance to accommodation and presbyopia", *Graefe's Arch Clin Exp. Ophthalmol.*, (1991) vol. 229, pp. 294-296.

Payne, Peter A. et al., "Ophthalmic Applications of Laser-Generated Ultrasound"; *SPIE*, vol. 3908, 2000, pp. 13-22.

Peterson, Jennifer A. et al., "Intraocular Pressure Measurement in Cynomolgus Monkeys, Tono-Pen Versus Manometry", *Investigative Ophthalmology & Visual Science*, 1996, vol. 37, No. 6, pp. 1197-1199.

Puliafito, Carmen A., M.D. et al., "High-Speed Photography of Excimer Laser Ablatio of the Cornea", *Arch Ophthalmol*, vol. 105, Sep. 1987, pp. 1255-1259.

Qian, Wen et al., "3 Year Simvastatin Treatment and Lens Nuclear Back Scattering"; *J Ophthalmol*, vol. 84, 2000, pp. 512-516.

Qian, Wen et al., "Universal Opacity Standard for Scheimpflug Photography", *Ophthalmic Res*, 2000, vol. 32, pp. 292-298.

Rafferty, Nancy et al., "Lens Wound Healing and Cataractogenesis in a Pigmented Eye", *Exp. Eye Res.* (1984) 38, 267-277.

Rao, Ch. Mohan, et al., "Level of Reduced Nucleotides and Lens Photo-damage", *National Eye Institute*, Bethesda, MD., p. 799.

Riley, Michael V., et al., "The Effects of UV-B Irradiation on the Corneal Endothelium", *Eye Research Institute of Oakland University*, 1987, pp. 1021-1033.

Ripken, T. et al., "FEM Simulation of the Human Lens Compared to Ex-Vivo Porcine Lens Cutting Pattern: A Possible Treatment of Presbyopia"; undated, 11 pgs.

Ripken T. et al., "First in-vivo studies of Presbyopia treatment with ultrashort laser pulses", *Proc. SPIE 5142*, vol. 137, 2003, p pgs.

Ripken, T. et al., "Fs-laser Induced Elasticity Changes to Improve Presbyopic Lens Accommodation", undated, 10 pgs.

Ripken T. et al., "Investigations for the correction of Presbyopia by fs-laser induced cuts", *Proc. SPIE 5314*, vol. 27, 2004, 9 pgs.

Rockwell, B.A. et al., "Safe Use of Ultra-short Lasers"; *SPIE*, vol. 3616, 1999, pp. 32-39.

Roesner, C.A.D. et al., "Light-Matter Interactions on the FEMTOSECOND Time Scale", *Department of Physics and Division of Engineering and Applied Sciences, Harvard University*; undated, pp. 1-27.

Rol, Pascal et al., "An Optomechanical Eye Model for Observation of Lens Photoablation"; *SPIE*, 1997, vol. 2971, pp. 171-174.

Sacks, Zachary S. et al., "Laser Spot Size as a Function of Tissue Depth and Laser Wavelength in Human Sclera", *SPIE*, 1998, vol. 3255, pp. 67-76.

Scammon, Richard J. et al., "Simulations of Shock Waves and Cavitation Bubbles Produced in Water by Picosecond and Nanosecond Laser Pulses", *SPIE*, 1998, vol. 3254, pp. 264-275.

Schachar, Ronald A. MD, PhD., et al., "A Revolutionary Variable Focus Lens", *Annals of Ophthalmology*, vol. 28, No. 1, Jan./Feb. 1996, pp. 11-18.

Schachar, Ronald A., M.D., "Cause and Treatment of Presbyopia With a Method for Increasing the Amplitude of Accommodation", *Annals of Ophthalmol*, 1992; 24:445-452.

Schachar, Ronald A., M.D. et al., "Experimental Destruction of Cataractous Lenses by Laser", *Ophthalmic Surgery*, Surgical Forum, pp. 506-509.

Schachar, Ronald A., M.D. et al., "Experimental Support for Schachar's Hypothesis of Accommodation", *Ann Ophthalmol*, 1993; 25: 404-409.

Schachar, Ronald A., MD, PhD, "Histology of the Ciliary Muscle-Zonular Connections", *Annals of Ophthalmology*, vol. 28, No. 2, Mar./Apr. 1996, 70-79.

Schachar, Ronald A. MD et al., "Mechanism of Human Accommodation as Analyzed by Nonlinear Finite Element Analysis", *Ann Ophthalmol*; 2001; vol. 33, No. 2, pp. 103-112.

Schachar, Ronald A., MD, PhD, "Pathophysiology of Accommodation and Presbyopia, Understanding the Clinical Implications",*J. Florida M.A.*, vol. 81, No. 4, Apr. 1994, pp. 268-271.

Schaeffel, Frank, "Kappa and Hirschberg Ratio Measured With an Automated Video Gaze Tracker", *Optometry and Vision Science*, 2002, vol. 79, No. 5, pp. 329-334.

Schaffer, Chris B. et al., "Dynamics of Femtosecond Laser-Induced Breakdown in Water From Femtoseconds to Microseconds", *Optics Express*, 2002, vol. 10, No. 3, pp. 196-203.

Schaffer, Chris B. et al., "Morphology of Femtosecond Laser-Induced Structural Changes in Bulk Transparent Materials", *Applied Physics Letters*, vol. 84, No. 9, 2004, pp. 1441-1443.

Shen, Nan; "Photodisruption in Biological Tissues Using Femtosecond Laser Pulses", *A Thesis Presented to the Department of Physics, Harvard University*, 2003, pp. 1-125.

Shen, Nan, et al., "Ablation of Cytoskeletal Filaments and Mitochondria in Live Cells Using a Femtosecond Laser Nanoscissor", *MCB*, 2005, vol. 2, No. 1, pp. 17-25.

Shen, Nan, et al., "Photodisruption in Biological Tissues and Single Cells Using Femtosecond Laser Pulses", undated, 2 pgs.

Shen, Nan, et al., "Surface and Bulk Photodisruption in Turbid Tissue Using Femtosecond Laser Pulses", *Department of Physics and Division of Engineering and Applied Sciences, Harvard University*, undated, pp. 1-24.

Sher, Neal A., MD, "Hyperopic Refractive Surgery", *Current Opinion in Ophthalmology*, 2001, vol. 12, pp. 304-308.

Sivak, Jacob G., "Through the Lens Clearly: Phylogeny and Development, The Proctor Lecture", *Ophthalmology & Visual Science*, 2004, vol. 45, No. 3, pp. 740-747.

Slingsby, Christine, "Lens Crystallin Crystal Structures", undated article. 3 pgs.

Söderberg, Per G., et al., "Angular Dependence of the Intensity of Back Scattered Light From Human Lenses With Nuclear Cataract, Implications for Measurement", *SPIE*, 2000, vol. 3908, pp. 34-37.

Söderberg, Per G., et al., "External Standard for Measurements with The Scheimpflug Slitlamp Microscope", *SPIE*, 1997, vol. 2971, pp. 8-13.

Solomon, Ira Seth, M.D., "Aqueous Humor Dynamics", undated, 17 pgs.

Spector, Abraham, "Aging of the Lens and Cataract Formation", *Aging and Human Visual Function*, pp. 27-43.

Srinivasan R. et al., "Excimer Laser Surgery of the Cornea", *American Journal of Ophthalmology*, vol. 96, 1993, pp. 710-715.

Srinivasan, R., "Ablation of Polymers and Biological Tissue by Ultraviolet Lasers", Oct. 1986, pp. 932-935.

Stitzel, Joel D., et al., "A Nonlinear Finite Element Model of the Eye With Experimental Validation for the Prediction of Globe Rupture", *Stapp Car Crash Journal*, 2002, vol. 45, 24 pgs.

Stitzel, Joel D., et al., "Blunt Trauma of the Aging Eye", *Arch Ophthalmol*, 2005, vol. 123, pp. 789-794.

Strauss, Moshe, et al., "Two-Dimensional Rayleigh Model of Vapor Bubble Evolution", *SPIE*, 1999, vol. 3601, pp. 212-224.

Strenk, Susan A., et al, "Age-Related Changes in Human Ciliary Muscle and Lens: A Magnetic Resonance Imaging Study", *Investigative Ophthalmology & Visual Science*, 1999, vol. 40, No. 6, pp. 1162-1169.

Strenk, Susan A., et al, "The Mechanism of Presbyopia", *Progress in Retinal and Eye Research*, 2004 vol. 11, pp. 1-15.

Strenk, Susan A. et al., "Magnetic Resonance Imaging Study of the Effects of Age and Accommodation on the Human Lens Cross-Sectional Area", *IOVS*, 2004, Vo. 45, No. 2, pp. 539-545.

Sweeney, Matthew H.J., et al., "Movement of Cysteine in Intact Monkey Lenses: The Major Site of Entry is the Germinative Region", *Experimental Eye Research*, 2003, vol. 77. pp. 245-251.

Swegmark, Gunnar, "Studies With Impedance Cyclography on Human Ocular Accommodation at Different Ages", *ACTA Ophthalmologica*, vol. 47, 1969, pp. 1186-1206.

Taboada, J. et al., "Response of the Corneal Epithelium to KrF Excimer Laser Pulses", *Health Physics*, vol. 30, 1981, pp. 677-683.

Taboada, J., et al., "Optically Coupled Technique for Photorefractive Surgery of the Cornea", *Optics Letters*, vol. 15, No. 9, May 1, 1990, pp. 458-460.

Tahi, Hassan, et al., "Restoring Accommodation: Surgical Technique and Preliminary Evaluation in Rabbits", *SPIE*, 1999, vol. 3591, pp. 267-269.

Tamm, Svenja, et al., "Age-Related Changes of the Human Ciliary Muscle. A Quantitative Morphometric Study",*Mechanisms of Aging and Development*, vol. 62, 1992, pp. 209-221.

Tang, Daxin; "Influence of Age, Diabetes, and Cataract on Calcium, Lipid-Calcium, and Protein-Calcium Relationships in Human Lenses", *Investigative Ophthalmology & Visual Science*, 2003, vol. 44, No. 5, pp. 2059-2066.

Taylor, Virginia L. et al., "Morphology of the Normal Human Lens", *Investigative Ophthalmology & Visual Science*, Jun. 1996, vol. 37, No. 7, pp. 1396-1410.

Topilow, Harvey W., M.D., "Vitreous Changes in Retinal Branch Vein Occlusion", *Arch Ophthalmol*, vol. 105, Sep. 1987.

Trokel, Stephen L., M.D., et al., "Excimer Laser Surgery of the Cornea", *American Journal of Ophthalmology*, vol. 96, No. 6, Dec. 1983, 710-715.

Tsai, Philbert S., "All-Optical, In-Situ Histology of Neuronal Tissue with Femtosecond Laser Pulses", *Imaging in Neuroscience and Development*, CSHL Press, undated, 12 pgs.

Tsubota, Kazuo, "Application of Erbium: YAG Laser in Ocular Ablation",*Ophthalmologica*, 1990, 200:pp. 117-122.

Van Alphen, G.W.H.M. et al., "Elasticity of Tissues Involved in Accommodation", *Vision Res.*, vol. 31, No. 7/8, 1991, pp. 1417-1438.

Venugopalan, V. et al., "The Thermodynamic Response of Soft Biological Tissues to Ultraviolet Laser Irradiation", *Biophysical Journal*, vol. 60, Oct. 1995, pp. 1258-1271.

Vilupuru, Abhiram S., "Spatially Variant Changes in Lens Power During Ocular Accommodation in a Rhesus Monkey Eye", *Journal of Vision*, 2004, vol. 4, pp. 299-309.

Vilupuru, Abhiram S., "Optical and Biometric Relationships of the Isolated Pig Crystalline Lens", *Ophthal. Physiol. Opt.*, 2001, vol. 21, No. 4, pp. 296-311.

Vogel, Alfred et al., "Factors Determining the Refractive Effects of Intrastromal Photorefractive Keratectomy with the Picosecond Laser", *J. Cataract Refract Surg.*, vol. 23, Nov. 1997, pp. 1301-1310.

Vogel, Alfred et al., "Interaction of Laser-Produced Cavitation Bubbles With an Elastic Tissue Model", *SPIE*, 2001, vol. 4257, pp. 167-177.

Vogel, Alfred et al., "Kinetics of Phase Transitions in Pulsed IR Laser Ablation of Biological Tissues", *SPIE*, 2003, vol. 4961, pp. 66-74.

Vogel, Alfred et al., "Laser-Induced Breakdown in the Eye at Pulse Durations From 80 ns to 100 fs", *SPIE*, 1998, vol. 3255, pp. 34-49.
Vogel, Alfred et al., "Numerical Simulation of Optical Breakdown for Cellular Surgery at Nanosecond to Femtosecond Time Scales", *SPIE*, 2001, vol. 4433, pp. 70-80.
Vrensen, G. F. J. M., "Aging of the human eye lens—A morphological point of view", *Comp. Biochem. Physiol.*, vol. 111A, 1995. pp. 519-553.
Waring III, George O., M.D., "Presbyopia and Accommodative Intraocular Lenses—the Next Frontier in Refractive Surgery?", *Refractive & Corneal Surgery*, vol. 8, Nov./Dec. 1992, pp. 421-423.
Weale, Robert D., SC., "Presbyopia Toward the End of the 20th Century", *Survey of Opthalmology*, vol. 34, No. 1, Jul.-Aug. 1989, pp. 15-29.
Werblin, Theodore P., M.D., "Should We Consider Clear Lens Extraction for Routine Refractive Surgery?", *Refractive & Corneal Surgery*, vol. 8, Nov./Dec. 1992, pp. 480-481.
Werner, Liliana, MD, et al., "Capsular Bag Opacification After Experimental Implantation of a New Accommodating Intraocular Lens in Rabbit Eyes", *J Cataract Refract Surg.*, 2004, vol. 30, pp. 1114-1123.
Werner, Liliana, MD. et al., "Posterior Capsule Opacification in Rabbit Eyes Implanted With 1-Piece and 3-Piece Hydrophobic Acrylic Intraocular Lenses", *J Cataract Refract Surg*, 2005, vol. 31, pp. 805-811.
Wyatt, Harry J., "Application of a Simple Mechanical Model of Accommodation to the Aging Eye", *Eye Res.*, vol. 33, No. 5/6, 1993, pp. 731-738.
Ziebarth, Nöel, et al; "Non-contact Optical Measurement of Lens Capsule Thickness During Simulated Accommodation", *SPIE*, 2005, vol. 5688, pp. 19-25.
Zuclich, Joseph A. et al., "A comparison of laser-induced retinal damage from infrared wavelengths to that from visible wavelengths", *Lasers and Light*, vol. 8, No. 1, 1997, pp. 15-29.
Zuclich, Joseph A. et al., "In Situ Measurements of Lens Fluorescence and its Interference With Visual Function", *Investigative Ophthalmology & Visual Science*, vol. 33, No. 2, 1993, pp. 410-415.
Zuclich, Joseph, "In Vivo Measurements of Optical Properties of the Ocular Lens", Reprinted from Proceedings of Ultraviolet Radiation Hazards, Jan. 26-27, 1994, *SPIE—The International Society for Optical Engineering*, Vo. 2134B Ultraviolet Radiation Hazards, 1994, pp. 99-112.
Zuclich, J.A., et al., "Ocular Effects of Penetrating IR Laser Wavelengths", Reprinted from Proceedings of Laser-Tissue Interaction VI, Feb. 6-9, 1995, *SPIE—The International Society for Optical Engineering*, vol. 2391, 1995, pp. 111-125.
Zuclich, Joseph A., et al., "Rapid Noninvasive Optical Characterization of the Human Lens", *Lasers in the Life Sciences*, 6(1), 1994, pp. 39-53.
Zuclich, Joseph A., "Research on the Ocular Effects of Laser Radiation", Technology Incorporated: *Life Sciences Division*.
Zuclich, Joseph A., "Ultraviolet-Induced Photochemical Damage in Ocular Tissues", *Health Physics*, vol. 56, No. 5, May 1989, pp. 671-681.
Zuclich, Joseph A., "Workshop on Long-Term Visual Health Risks of Optical Radiation—Thermal Cataracts Induced by UV Laser Radiation", *Workshop Report, Cataract Working Group*. Search Reports.
International Search Report dated Sep. 25, 2007 from related PCT application No. PCT/US07/01262, 1 page.
International Search Report dated Oct. 4, 2007 from related PCT application No. PCT/US07/01486, 1 page.
International Search Report dated Oct. 23, 2007 from related PCT application No. PCT/US07/01312, 1 page.
International Search Report dated Jan. 2, 2008 from related PCT application No. PCT/US07/01353, 1 page. Abstracts.
Faraggi, E. et al., "Stress confinement, shock wave formation and laser induced damage", Conference 5695: Optical Interactions with Tissue and Cells XVI, *Photonics West*, undated, 1 pg.
Fisher, R F, "The ciliary body in accommodation", *Trans Ophthalmol. Soc. UK*, 1989, vol. 105,1 pg.
Fisher, RF. "The mechanics of accommodation in relation to presbyopia", *Eye*, 1988, vol. 2 1 pg.

Garner, LF et al., "Changes in equivalent and gradient refractive index of the crystalline lens with accommodation", *Optom Vis. Sci.*, 1997, vol. 74,1 pg.
Garner LF et al., "Changes in ocular dimensions and refraction with accommodation", *Ophthalmic Physiol. Opt.*, 1997, vol. 17, 1 pg.
Helsterkamp, A. et al., "Nanosurgery in live cells using ultrashort laser pulses", Conference 5695: Optical Interactions with Tissue and Cells XVI, *Photonics Wes*, undated, 1 pg.
Kuszak, J.R., "Progressively More Complex Star Sutures Formed in Primate Lenses During Periods of Development, Growth and Aging Are Related to Accommodation", *Abstracts Online*, obtained from the Internet on Apr. 19, 2006 at: http://www.abstractsonline.com/viewer/viewAbstractPrintFriendly.asp?CKey={C8FDF5D . . . Apr. 19, 2006, I page.
McBrien NA et al., "Experimental myopia in a diurnal mammal (*Sciurus carolinensis*) with no accommodative ability", *J Physiol.*, 1993, vol. 469, 1 pg.
McCourt ME et al., "Refractive state, depth of focus and accommodation of the eye of the California ground squirrel (*Spermophilus beecheyi*)", *Vision Res.*, 1984, vol. 24, 1 pg.
Prokofeva GL et al., Effects of low-intensity infrared laser irradiation on the eye an experimental study, *Vestn Oftalmol.*, 1996, vol. 112, 1 pg.
Rafferty, NS et al., "Comparative study of actin filament patterns in lens epithelial cells, Are these determined by the mechanisms of lens accommodation?", *Curr Eye Res.*, 1989, vol. 8, 1 pg.
Roa, Ch. Mohan et al., "Level of Reduced Nucleotides and Lens Photodamage", *National Eye Institute*, undated, 1 pg.
Van Alphen GW et al., "Elasticity of tissues involved in accommodation", *Vision Res.*, 1991, vol. 31, 1 pg.
Wang, B. et al., "In-vivo animal studies on intraocular nanosurgery with low-energy 80 MHZ near infrared femtosecond laser pulses", Conference 5695: Optical Interactions with Tissue and Cells XVI, *Photonics West*, undated, 1 pg. Presentation Materials.
Avro, "Statement for the Use of Animals in Ophthalmic and Visual Research", *The Association for Research in Vision and Ophthalmology*, copyright © 2002, obtained from the Internet on Jan. 15, 2005 at: http://www.avro.org/AboutAvro/animalst.asp, 3 pgs.
Gattass, Rafael et al., "Femtosecond laser micromaching Applications in Technology and Biology", Photonics West conference Jan. 2005, 78 pgs.
Hermans, E. et al., "Estimating the External Force Acting on the Human Eye Lens During Accommodation Using Finite Elements Modeling", presentation on Accommodation & Presbyopia, May 2005, 1 pg.
Kuszak et al., "Light, scanning and electron micrographs have lead to the following interpretations of secondary fiber formation", 2004, 16 pgs.
Lubatschowski, H. et al., "Treatment of Presbyopia by Cutting the Cystaline Lens: A Comparison of FEM Simulation and Ex vivo Studies", *Lazer Zentrum Hannover e.V.*
Mazur, Eric, "An Introduction to Femtosecond Laser Science", Photonics West conference Jan. 2005, 291 pgs.
Nebel, Achim et al., "Fast Micromachining using Picosecond Lasers", Photonics West conference Jan. 2005, 37 pgs.
OSN SuperSite, "Increase in lens stiffness with age may cause presbyopia, study suggests", 2005, 1 pg.
"Principles of Ultrafast Laser Surgery Femtosecond Laser-Tissue Interaction", copyright © Center for Ultrafast Optical Sciences, Un. of Michigan, undated, 3 pgs.
"Presbyopia—preconditions", *Laser Zentrum Hannover*, undated, 11 pgs.
Roudy, Carlos—"Propagation factor qualifies leaser bean performance", *Laser World Focus*, undated, 3 pgs.
Shen, J. et al. "Measurement of the Lens Capsule Contraction Force in the Radial Direction", presentation on Accommodation & Presbyopia, May 2005, 1 pg.
Figure 4.2—Optical constants for a "standard eye", undated, 1 pg.
Picture of an eye obtained from the Internet on Mar. 28, 2005 at: http://www.opt.uh.edu/research/aglasser/aao/gonioani.gif, 1 pg.
Pictures of eyes, 5 pgs.
Loesel paper graphs, 2 pgs.

CD-ROM containing copies of seven videos relating to eyes: 1. AG.MOV 2. Glasser.WMV 3. Kuszak & Zoltoski movie1.mov 4. Kuszak & Zoltoski movie2.mov 5. Kuszak & Zoltoski movie3.mov 6. VidepClip1.mov 7. VideoClip2.mov.

Optical Radiation and Visual Health, pp. 28-33.

Gills, James P., "Treating astigmatism at the time of cataract surgery", *Current Opinion in Ophthalmology*, 2002, vol. 13, p. 2-6.

Lubatschowski, Holger, "Surgical Laser System for the Treatment of Presbyopia", *7th Biotech in Europe Investor Forum*, Switzerland, 2007, 9 pgs.

Nichamin, Louis D., "Treating astigmatism at the time of cataract surgery", *Current Opinion in Ophthalmology*, 2003, vol. 14, p. 35-38.

Agrahari, S. et al., "The Potential of Photodisruption Laser Treatment of the Crystalline Lens to Rupture the Lens Capsule", *ARVO Abstract* No. 07-A-6800, 2006, 1 pg.

Frey, R. W. et al., "Modification of Lens Mechanics of Human Cadaver and Porcine Lenses Using Photodisruption Laser to Change Lens Power and Increase Flexibility", *ARVO Abstract* No. 07-A-06652, 2006, 1 pg.

Gray, G. et al., "Constructions of a Computer Mesh Model of the Anatomical Human Crystalline Lens Fiber Ultrastructure", *ARVO Abstract*, 2006, 1 pg.

Kuszak, J. R. et al., "Results From a Finite Element Model Analysis of the Accommodative Process Based on the Human Crystalline Lens Fiber Ultrastructure", *ARVO Abstract*, 2006, 1 pg.

Oberheide, U. et al., "Flexibility Increase of Human Donor Lenses After Femosecond Laser Treatment (fs-Lentotomy)", *ARVO Abstract* No. 3833/B571, 2007, 2 pgs.

Olmstead, T. et al., "The Use of an Off Axis Slit Laser Camera System for Determining Photodisruptive Laser Placement in Lenses", *ARVO Abstract* No. 07-A-5967, 2006, 1 pg.

Subramaniam, H. et al., "Finite Element Analysis of the Accommodative Process in the Whole Globe", *ARVO Abstract* No. 07-A-6249, 2006, 1 pg.

Yeilding, R. H. et al., "Lens Culture System for Long Term Study of Porcine Lenses Pre and Post Laser Photodisruption Treatment", *ARVO Abstract* No. 01-A-6495, 2006, 1 pg.

Zepkin, N. et al., "Measurement of Temperature Rise in Porcine Crystalline Lenses from a Photodisruption Laser", *ARVO Abstract* No. 07-A-6709, 2006, 1 pg.

Zoltoski, R. K. et al., "Reverse Engineering of Human Lenses", *ARVO Abstract* No. 2018/B159, 2007, 2 pgs.

Agrahari, S. et al., "The Potential of Photodisruption Laser Treatment of the Crystalline Lens to Rupture the Lens Capsule", *ARVO* No. B574 # 3936, 2007, 1 pg.

Frey, R. W. et al., "Modification of Lens Mechanics of Human Cadaver and Porcine Lenses Using Photodisruption Laser to Change Lens Power and Increase Flexibility", *ARVO* No. B572 # 3834, 2007, 1 pg.

Gray, G. et al., "Constructions of a Computer Mesh Model of the Anatomical Human Crystalline Lens Fiber Ultrastructure", *ARVO* No. B567 # 3289, 2007, 1 pg.

Kuszak, J. R. et al., "Results From a Finite Element Model Analysis of the Accommodative Process Based on the Human Crystalline Lens Fiber Ultrastructure", *ARVO* No. B963 # 988, 2007, 1 pg.

Olmstead, T. et al., "The Use of an Off Axis Slit Laser Camera System for Determining Photodisruptive Laser Placement in Lenses", *ARVO* No. B573 # 3835, 2007, 1 pg.

Yeilding, R. H. et al., "Lens Culture System for Long Term Study of Porcine Lenses Pre and Post Laser Photodisruption Treatment", *ARVO* No. B576 # 3838, 2007, 1 pg.

Zepkin, N. et al., "Measurement of Temperature Rise in Porcine Crystalline Lenses from a Photodisruption Laser", *ARVO* No. B575 # 3837, 2007, 1 pg.

Neev, Joseph, "Ultrashort Pulse Lasers: A New Tool for Biomedical Applications", *SPIE*, vol. 3255, 1998, pp. 2-7.

O'Donnell, Colleen B., et al., "Ablation Smoothness as a Function of Excimer Laser Delivery System", *J. Cataract Refract Surg.*, vol. 22, Jul./Aug. 1996, pp. 682-685.

Parel, Jean-Marie et al., "Intraocular Implants for the Surgical Correction of Presbyopia"; *In Ophthalmic Technologies X*, Proceedings of SPIE, vol. 3908, 2000, pp. 115-122.

Patel, C.K. et al., "The Ageing Lens", *Association of Optometrists, City University, London*, May 4, 2011, undated, www.optometry.co.uk, pp. 27-31.

Puliafito, Carmen A., M.D. et al., "High-Speed Photography of Excimer Laser Ablation of the Cornea", *Arch Ophthalmol*, vol. 105, Sep. 1987, pp. 1255-1259.

Ripken, T. et al., "FEM Simulation of the Human Lens Compared to Ex-Vivo Porcine Lens Cutting Pattern: A Possible Treatment of Presbyopia", *Proc. SPIE*, vol. 6138, 2006, 11 pgs.

Ripken T. et al., "First in-vivo studies of Presbyopia treatment with ultrashort laser pulses", *Proc. SPIE 5142*, vol. 137, 2003, pp. 137-145.

Ripken, T. et al., "Fs-laser Induced Elasticity Changes to Improve Presbyopic Lens Accommodation", *Proc. SPIE*, vol. 5638, 2005, pp. 278-287.

Ripken T. et al., "Investigations for the correction of Presbyopia by fs-laser induced cuts", *Proc. SPIE 5314*, vol. 27, 2004, pp. 27-35.

Schachar, Ronald A., M.D., "Cause and Treatment of Presbyopia With a Method for Increasing the Amplitude of Accommodation", *Annals of Ophthalmol*, 1992, vol. 24, pp. 445-452.

Schachar, Ronald A., M.D. et al., "Experimental Support for Schachar's Hypothesis of Accommodation", *Ann Ophthalmol*, 1993, vol. 25, pp. 404-409.

Schachar, Ronald A., MD, PhD, "Histology of the Ciliary Muscle-Zonular Connections", *Annals of Ophthalmology*, vol. 28, No. 2, Mar./Apr. 1996, pp. 70-79.

Schaffer, Chris B. et al., "Dynamics of Femtosecond Laser-Induced Breakdown in Water From Femtoseconds to Microseconds", *Optics Express*, Feb. 11, 2002, vol. 10, No. 3, pp. 196-203.

Schaffer, Chris B. et al., "Morphology of Femtosecond Laser-Induced Structural Changes in Bulk Transparent Materials", *Applied Physics Letters*, vol. 84, No. 9, Mar. 1, 2004, pp. 1441-1443.

Shen, Nan; "Photodisruption in Biological Tissues Using Femtosecond Laser Pulses", *A Thesis Presented to the Department of Physics, Harvard University*, Jan. 2003, pp. 1-125.

Sivak, Jacob G., "Through the Lens Clearly: Phylogeny and Development, The Proctor Lecture", *Investigative Ophthalmology & Visual Science*, Mar. 2004, vol. 45, No. 3, pp. 740-747.

Slingsby, Christine, "Lens Crystallin Crystal Structures", Nov. 13, 2009, 3 pgs.

Söderberg, Per G., et al., "External Standard for Measurements with the Scheimpflug Slitlamp Microscope", *SPIE*, vol. 2971, 1997, pp. 8-13.

Solomon, Ira Seth, M.D., "Aqueous Humor Dynamics", 2002, 17 pgs.

Stitzel, Joel D., et al., "A Nonlinear Finite Element Model of the Eye With Experimental Validation for the Prediction of Globe Rupture", *Stapp Car Crash Journal*, vol. 46, Nov. 2002, pp. 81-102.

Strauss, Moshe, et al., "Two-Dimensional Rayleigh Model of Vapor Bubble Evolution", *SPIE*, vol. 3601, Jan. 1999, pp. 212-224.

Strenk, Susan A., et al, "Age-Related Changes in Human Ciliary Muscle and Lens: A Magnetic Resonance Imaging Study", *Investigative Ophthalmology & Visual Science*, May 1999, vol. 40, No. 6, pp. 1162-1169.

Tamm, Svenja, et al., "Age-Related Changes of the Human Ciliary Muscle. A Quantitative Morphometric Study", *Mechanisms of Aging and Development*, vol. 62, 1992, pp. 209-221.

Topilow, Harvey W., M.D., "Vitreous Changes in Retinal Branch Vein Occlusion", *Arch Ophthalmol*, vol. 105, Sep. 1987, pp. 1164-1165.

Trokel, Stephen L., M.D., et al., "Excimer Laser Surgery of the Cornea", *American Journal of Ophthalmology*, vol. 96, No. 6, Dec., 1983, pp. 710-715.

Tsai, Philbert S., "All-Optical, In-Situ Histology of Neuronal Tissue with Femtosecond Laser Pulses", *Imaging in Neuroscience and Development*, CSHL Press, undated, pp. 1-12.

Tsubota, Kazuo, "Application of Erbium: YAG Laser in Ocular Ablation", *Ophthalmologica*, 1990, Vol, 200, pp. 117-122.

Werner, Liliana, MD, et al., "Capsular Bag Opacification After Experimental Implantation of a New Accommodating Intraocular Lens in Rabbit Eyes", *J Cataract Refract Surg.*, May 2004, vol. 30, pp. 1114-1123.

Zuclich, Joseph A. et al., "In Situ Measurements of Lens Fluorescence and its Interference With Visual Function", *Investigative Ophthalmology & Visual Science*, vol. 33, No. 2, Feb. 1992, pp. 410-415.

Zuclich, Joseph, "In Vivo Measurements of Optical Properties of the Ocular Lens", Reprinted from Proceedings of Ultraviolet Radiation Hazards, Jan. 26-27, 1994, *SPIE-The International Society for Optical Engineering*, Vo. 2134B Ultraviolet Radiation Hazards, 1994, pp. 99-112.

Zuclich, Joseph A., et al., "Rapid Noninvasive Optical Characterization of the Human Lens", *Lasers in the Life Sciences*, vol. 6, No. 1, 1994, pp. 39-53.

Zuclich, Joseph A., "Research on the Ocular Effects of Laser Radiation", *Technology Incorporated: Life Sciences Division*, pp. 6-1 to 6-4; 7-1 to 7-23; 8-1 to 8-8; 9-1 to 9-12; 10-1 to 10-9, date unknown.

Zuclich, Joseph A., "Workshop on Long-Term Visual Health Risks of Optical Radiation—Thermal Cataracts Induced by UV Laser Radiation", *Workshop Report, Cataract Working Group*, date unknown, 13 pgs. Abstracts.

Faraggi, E. et al., "Stress confinement, shock wave formation and laser induced damage", Conference 5695: Optical Interactions with Tissue and Cells XVI, *Photonics West*, Jan. 2006, 1 pg.

Fisher, R F, "The ciliary body in accommodation", *Trans Ophthalmol. Soc. UK*, 1986, vol. 105,1 pg.

Fisher, RF. "The mechanics of accommodation in relation to presbyopia", *Eye*, 1988, vol. 2, 1 pg.

Garner, LF et al., "Changes in equivalent and gradient refractive index of the crystalline lens with accommodation", *Optom Vis. Sci.*, Jan. 1997, vol. 74,1 pg.

Garner LF et al., "Changes in ocular dimensions and refraction with accommodation", *Ophthalmic Physiol. Opt.*, Jan. 1997, vol. 17, 1 pg.

Helsterkamp, A. et al., "Nanosurgery in live cells using ultrashort laser pulses", Conference 5695: Optical Interactions with Tissue and Cells XVI, *Photonics West*, undated, 1 pg.

Kuszak, J.R., "Progressively More Complex Star Sutures Formed in Primate Lenses During Periods of Development, Growth and Aging Are Related to Accommodation", *Abstracts Online*, obtained from the Internet on Apr. 19, 2006 at: http://www.abstractsonline.com/viewer/viewAbstractPrintFriendly.asp?CKey={C8FDF5D . . Apr. 19, 2005, 1 page.

Rao, Ch. Mohan et al., "Level of Reduced Nucleotides and Lens Photodamage", *National Eye Institute*, undated, 1 pg.

ARVO, "Statement for the Use of Animals in Ophthalmic and Visual Research", *The Association for Research in Vision and Ophthalmology*, copyright © 2002, obtained from the Internet on Jan. 15, 2005 at: http://www.avro.org/AboutAvro/animalst.asp, 3 pgs.

Gattass, Rafael et al., "Femtosecond laser micromachining Applications in Technology and Biology", Photonics West conference Jan. 2005, 78 pgs.

Lubatschowski, H. et al., "Treatment of Presbyopia by Cutting the Cystaline Lens: A Comparison of FEM Simulation and Ex vivo Studies", *Lazer Zentrum Hannover e. V*, publication date unknown, 22 pgs.

"Presbyopia —preconditions", *Laser Zentrum Hannover*, undated, 11 pgs.

Roundy, Carlos—"Propagation factor qualifies leaser bean performance", *Laser World Focus*, 1999, 3 pgs.

Pictures of eyes, date and published unknown, 5 pgs.

Loesel paper graphs, date and publisher unknown, 4 pgs.

Akchurin, Garif et al., "Evaluation of the degree of turbidity if cataract lens and its correlation with retinal visual acuity", *SPIE*, vol. 3591, Jan. 1999, pp. 74-81.

Al-Ghoul, K. J. et al., "Distribution and Type of Morphological Damage in Human Nuclear Age-Related Cataracts", *Department of Cell Biology and Anatomy, University of North Carolina and Duke University Eye Center*, 1996, pp. 237-251.

Alio, et al., "Crystalline Lens Optical Dysfunction through Aging", *Ophthalmology*, vol. 112, No. 11, Nov. 2005, pp. 2022-2029.

Amann, Josef et al., "Increased Endothelial Cell Density in the Paracentral and Peripheral Regions of the Human Cornea", *American Journal of Ophthalmology*, vol. 135, No. 5, May 2003, pp. 584-590.

Amendt, M. Strauss et al., "Modeling of bubble dynamics in relation to medical applications", *Proc. of SPIE*, vol. 2975, 1997, pp. 362-373.

Ansari, Rafat R. et al., "Measuring lens opacity: combining quasi-elastic light scattering with Scheimpflug imaging system", *Proc. of SPIE*, vol. 3246, 1998, pp. 35-42.

Apple, David J. et al., "Preparation and Study of Human Eyes Obtained Postmortem with the Miyake Posterior Photographic Technique", *Ophthalmology*, vol. 97, No. 6, Jun. 1990, pp. 810-816.

Armstrong, Larry "A cataract Breakthrough May Be on the Way", *Business Week*, Mar. 23, 1998, pp. 90-92.

Aston, Adam, "Why Settle for 20/20?", *Business Week*, Mar. 17, 2003, pp. 95-96.

Azzam, Naiel et al., "Long-term lens organ culture system to determine age-related effects of UV irradiation on the eye lens", *Experimental Eye Research*, vol. 79, 2004, pp. 903-911.

Back, Arthur P. et al., "Correction of Presbyopia with Contact Lenses: Comparative Success Rates with Three Systems", *Optometry & Vision Science*, vol. 66, No. 8, 1989, pp. 518-525.

Balaram, Mini et al., Noncontact Specular Microscopy of Human Lens Epithelium, *IOVS*, vol. 41, No. 2, Feb. 2000, pp. 474-481.

Barak, Adiel et al., "Anterior capsulotomy using the $CO_2$ laser", *Proc. of SPIE*, vol. 3246, 1998, pp. 196-198.

Bath, Patricia E. et al., "Endocapsular Excimer Laser Phakoablation Through a 1-mm Incision", *Opthalmic Laser Therapy*, vol. 2, No. 4, 1987, pp. 245-249.

Beers, A. P. A. et al. "Age-Related Changes in the Accommodation Mechanism", *Optometry and Vision Science*, vol. 73, No. 4, 1996, pp. 235-242.

Beers, A. P. A. et al., "In Vivo Determination of the Biomechanical Properties of the Component Elements of the Accommodation Mechanism", *Vision Res.*, vol. 34, 1994, pp. 2897-2905.

Bellows, John G., M.D. et al., "B. Cataracta Complicata", *Traumatic Cataract*, undated but prior to Jul. 2009, pp. 270-272.

Ben-Sira, I. et al., "Clinical method for measurement of light back scattering from the in vivo human lens", *Invest. Ophthalmol. Vis. Sci.*, vol. 19, No. 4 (Reports), Apr. 1980, pp. 435-437.

Bettelheim, Frederick A. et al., "Syneretic Response of Aging Normal Human Lens to Pressure", *Investigative Ophthalmology & Visual Science*, vol. 44, No. 1, Jan. 2003, pp. 258-263.

Bigler, Emmanuel, "Depth of field and Scheimpflug's rule: a "minimalist" geometrical approach", published unknown, 2002, pp. 1-17.

Billie, J. F. et al., "3D Imaging of the Human Eye Using the laser Tomographic Scanner Lts", publisher unknown, undated but prior to Jul. 2009, 2 pgs.

Bito, L.Z. et al., "Age-dependent loss of accommodative amplitude in rhesus monkeys: an animal model for presbyopia", *Invest. Ophthalmol. Vis. Sci.*, vol. 23, No. 1, Jul. 1982, pp. 23-31.

Bor, Zs. PhD., et al., "Plume Emission, Shock Wave and Surface Wave Formation During Excimer Laser Ablation of the Cornea", *Supplement to Retroactive & Corneal Surgery*, vol. 9, Mar./Apr. 1993, pp. S111-S115.

Borja, David et al., "Crystalline Lens MTF Measurement During Simulated Accommodation", *Proc. of SPIE*, vol. 5688, 2005. pp. 26-32.

Borkman, Raymond F. et al., "Evidence for a Free Radical Mechanism in Aging and u.v.—Irradiated Ocular Lenses", *Exp. Eye Res.*, 1977, vol. 25, pp. 303-309.

Braham, Lewis, "Eye Surgery: It's Getting Sharper", *Business Week*, Oct. 18, 2004, pp. 142-143.

Breitenfeld, P. et al., "Finite Element Method—Simulation of the Human Lens During Accommodation", publiasher unknown, vol. 5863, 2005, 9 pgs.

Breitling, Detlef et al., "Fundamental aspects in machining of metals with short and ultrashort laser pulses", *Proc. of SPIE*, vol. 5339, 2004, pp. 1-15.

Bron, A.J., "The Ageing Lens", *Opthalmologics*, vol. 214, 2000, pp. 86-104.

Brown, Nicholas, "Dating the onset of cataract", *Transactions of the Ophthalmological Society of the United Kingdom*, vol. 96, 1976, pp. 18-23.

Brown, Nicholas "The Change in Lens Curvature with Age", *Exp. Eye Res.*, vol. 19, 1974, pp. 175-183.

Burd, H.J. et al., "Can reliable values of Young's modulus be deduced from Fisher's (1971) spinning lens measurements?", *Vision Research*, volume unknown, 2005, pp. 1-15.

Campbell, Melanie C. W., "Measurement of Refractive Index in an Intact Crystalline Lens", *Vision Research*, vol. 24, No. 5, 1984, pp. 409-415.

Carey, James et al., "Propagation and Characterization of Ultrashort Laser Pulses", Harvard University, 2003, pp. 1-30.

Charles, M. W. et al., "Dimensions of the Human Eye Relevant to Radiation Protection", *Phys. Med. Biol.*, 1975, vol. 20, No. 2, © 1975, pp. 202-218.

Chen, Wei-Li et al., Ultrasound Biomicroscopic Findings in Rabbit Eyes Undergoing Scleral Suction during Lamellar Refractive Surgery, *IOVS*, vol. 43, No. 12, Dec. 2002, pp. 3665-3672.

Coleman, D. Jackson et al., "Presbyopia, Accommodation, and the Mature Catenary", *Ophthalmology*, vol. 108, No. 9, Sep. 2001, pp. 1544-1551.

Cook, Christopher A. et al., "Aging of the Human Crystalline Lens and Anterior Segment", *Vision Res.*, vol. 34, No. 22, 1994. pp. 2945-2954.

Costagliola, Ciro et al., "ArF 193 nm Excimer Laser Corneal Surgery as a Possible Risk Factor in Cataractogenesis", *Exp. Eye Res.*, vol. 58, 1994. pp. 453-457.

Cotlier, Edward, M.D., "The Lens", *Adler's Physiology of the Eye*, copyright 2003, pp. 268-290.

Crawford, Kathryn S. et al., "The Role of the Iris in Accommodation of Rhesus Monkeys", *Investigative Ophthalmology & Visual Science*, vol. 31, No. 10, Oct. 1990, pp. 2185-2190.

Croft, Mary Ann et al., "Accommodation and Presbyopia", publisher unknown, vol. 41, 2001, pp. 33-46.

Croft, Mary Ann et al., "Accommodation and Presbyopia: The Ciliary Neuromuscular View", *Opthalmol Clin N Am*, vol. 19, 2006, pp. 13-24.

Croft, Mary Ann et al., Accommodative Ciliary Body and Lens Function in Rhesus Monkeys, I: Normal Lens, Zonule and Ciliary Process Configuration in the Iridectomized Eye, *IOVS*, vol. 47, No. 3, Mar. 2006, pp. 1076-1086.

Croft, Mary Ann et al., "The Zonula, Lens, and Circumlental Space in the Normal Iridectomized Rhesus Monkey Eye", *IOVS*, vol. 47, No. 3, Mar. 2006, pp. 1087-1095.

Cromie, William J., "Laser Makes History's Fastest Holes", *The Harvard University Gazette*, 1999, obtained at: http://www.news.harvard.edu/gazette/1999/10.07/laser.html, 6 pags.

Datta, Debajyoti, "Tissue Surgery and Subcellular Photodisruption with Femtosecond Laser Pulses", *Thesis for Dept. of Physics*, Harvard University, May 2002, pp. 1-74.

Dausinger, Friedrich et al., "Micro-machining with ultrashort laser pulses: From basic understanding to technical applications", publisher unknown, undated but prior to Jul. 2009, pp. 1-10.

Douven, Lucien F.A. et al., "Characterization of Mechanical Behaviour of Human Skin In Vivo", *Proc. of SPIE*, vol. 3914, 2000, pp. 618-629.

Ehrmann, Klaus et al., "Evaluation of porcine crystalline lenses in comparison with molded polymer gel lenses with an improved ex vivo accommodation simulator", *Proc. of SPIE*, vol. 5688, 2005, pp. 240-251.

Ehrmann, Klaus et al., "Ex Vivo Accommodation Simulator II—Concept and Preliminary Results", *Proc. of SPIE*, vol. 5314, 2004, pp. 48-58.

El-Osta, Austen A.R. et al., "In vitro model for the study of human posterior capsule opacification", *J Cataract Refract Surg*, vol. 29, 2003, pp. 1593-1600.

Erpelding, Todd N. et al., "Bubble-Based Acoustic Radiation Force for Monitoring Intraocular Lens Elasticity", *IEEE Intl Ultrasonics Symposium*, volume unknown, 2004, pp. 732-735.

Fagerholm, Per P.P., "The Response of the Lens to Trauma", *Trans. Ophtal. Soc. U. K.*, 1982, vol. 102, pp. 369-374.

Farnsworth, P.N. et al., "Anterior Zonular Shifts with Age", *Exp. Eye Res.*, vol. 28, 1979, pp. 291-297.

Findl, Oliver et al., "Laserinterferometric Assessment of Pilocarpine-Induced Movement of an Accommodating Intraocular Lens—A Randomized Trial", *Ophthalmology*, vol. 111, No. 8, Aug. 2004, pp. 1515-1521.

Fisher, R.F. et al., "Changes in lens fibres after damage to the lens capsule", publisher unknown, undated but prior to Jul. 2009, 4 pgs.

Fisher, R. F., "The Ciliary Body in Accommodation", *Trans. Opthalmol. Soc. U.K.*, vol. 105, 1986, pp. 208-219.

Fisher, R. F. et al., "The elastic constants and ultrastructural organization of a basement membrane (lens capsule)", *Proc. R. Soc. Lond. B.*, vol. 193, 1976, pp. 335-358.

Fisher, R.F., "The Elastic Constants of the Human Lens", *J. Physiol.*, vol. 212, 1971, pp. 147-180.

Fisher, R.F., "Elastic Constants of the Human Lens Capsule", *J. Physiol.*, vol. 201, 1969, pp. 1-19.

Fisher, R. F., "The Mechanics of Accommodation in Relation to Presbyopia", *Eye*, vol. 2, 1988, pp. 646-649.

Fleck, Brian W. et al., "Q-switched Nd:YAG laser disruption of rabbit lens nucleus", *Laser and Light in Ophthalmology*, vol. 3. No. 3, 1990, pp. 227-232.

Foster, C. Stephen et al., "Smolin and Thoft's the Cornea: Scientific Foundations and Clinical Practice", *The New England Journal of Medicine*, vol. 353 No. 23, 2005, pp. 2519-2520.

Fujimoto, James et al., "Biomedical Optics", Photonics West, *Proc. of SPIE*, Vol. unknown, 2005, pp. 23-70.

Gayen, Tapan K. et al., "Near-infrared laser welding of aortic and skin tissues and microscopic investigation of welding efficacy", *Proc. of SPIE*, vol. 4949, 2003, pp. 182-185.

Gershenzon, A. et al., "Clinical and Epidemiology—New software for lens retro-illumination digital image analysis", *Australian and New Zealand Journal of Ophthalmology*, vol. 27, 1999, pp. 170-172.

Giblin, Frank J. et al., "Nuclear Light Scattering, Disulfide Formation and Membrane Damage in Lenses of Older Guinea Pigs Treated with Hyperbaric Oxygen", *Exp. Eye Res.*, vol. 60, 1995, pp. 219-235.

Gimbel, Howard V. et al., "Intrastromal Photorefractive Keratectomy with the Nd:YLF Laser", publisher unknown, vol. 34, Iss. 4, 1994, pp. 139-145.

Glasser, Adrian et al., "Accommodative Changes in Lens Diameter in Rhesus Monkeys", *IOVS*, vol. 47, No. 1, Jan. 2006, pp. 278-286.

Glasser, Adrian et al., "On modeling the causes of presbyopia", *Vision Research*, vol. 41, 2001, pp. 3083-3087.

Glasser, Adrian et al., "Presbyopia and the Optical Changes in the Human Crystalline Lens with Age", *Vision Res.*, vol. 38, No. 2, 1998, pp. 209-229.

Glasser, Adrian et al., "Ultrasound Biomicroscopy of the Aging Rhesus Monkey Ciliary Region", *Optometry and Vision Science*, vol. 78, No. 6, 2001, pp. 417-424.

Grace, Jeffery M. et al., "Repetitively Pulsed Ruby Lasers As Light Sources for High-Speed Photography", *Optical Engineering*, vol. 37, No. 8, Aug. 1998, pp. 1-26.

Gwon, Arlene et al., "Focal laser photophacoablation of normal and cataractous lenses in rabbits: Preliminary report", *J Cataract Refract Surg*, vol. 21, May 1995, pp. 282-286.

Habib, Maged S. et al., "Myopic Intrastromal Photorefractive Keratectomy With the Neodymium-Yttrium Lithium Fluoride Picosecond Laser in the Cat Cornea", *Arch Ophthalmol.*, vol. 113, Apr. 1995, pp. 499-505.

Hahn, D.W., "Dynamics of Ablation Plume Particles Generated During Excimer Laser Corneal Ablation", *Lasers in Surgery and Medicine*, vol. 16, 1995, pp. 384-389.

Hamaoui, Marie et al., "Ex-vivo testing of crystalline lens substitutes: a pilot study", *Proc. of SPIE*, vol. 3908, 2000, pp. 123-130.

Hammer, Daniel X. et al., "Dual OCT/SLO Imager with Three-Dimensional Tracker", *Proc. of SPIE*, vol. 5688, 2005, pp. 33-44.

Hara, Tsutomu, M.D. et al., "Complications associated with endocapsular balloon implantation rabbit eyes", *J Cataract Refract Surg*, vol. 20, Sep. 1994, pp. 507 and 512.

Harding, J. J., "Disulphide Cross-linked Protein of High Molecular Weight in Human Cataractous Lens", *Exp. Eye Res.*, vol. 17, 1973, pp. 377-383.

Hartwick, Andrew T. E. et al., "Ephitelial activity of hexokinase and glucose-6-phosphate dehydrogenase in cultured bovine lenses recovering from pharmaceutical-induced optical damage", *Molecular Vision*, vol. 9, 2003, pp. 594-600.

Heisterkamp, Alexander et al., "Nonlinear effects inside corneal tissue after fs-photodisruption", *Proc. of SPIE*, vol. 4433, 2001, pp. 55-60.

Heisterkamp, Alexander et al., "Pulse energy dependence of subcellular dissection by femtosecond laser pulses", *Optics Express*, vol. 13, No. 10, May 2005, pp. 3690-3696.

Hemenger, Richard P. et al., "Change With Age of the Refractive Index Gradient of the Human Ocular Lens", *Investigative Ophthalmology & Visual Science*, Mar. 1995, vol. 36, No. 3. pp. 703-707.

Heys, Karl Robert et al., "Massive increase in the stiffness of the human lens nucleus with age: the basis for presbyopia?",*Molecular Vision*, vol. 10, 2004, pp. 956-963.

Ho, A. et al., "Feasibility of simultaneous correction of ametropia by varying gel refractive index with phaco-ersatz", *Proc. of SPIE*, vol. 4245, 2001, pp. 119-128.

Hoffman, Richard S. et al., "Refractive lens exchange as a refractive surgery modality", Copyright © 2004 Lippincott Williams & Wilkins, pp. 22-28.

Holzer, Mike P. et al., "Corneal flap complications in refractive surgery—Part 1: Development of an experimental animal model", *J Cataract Refract Surg*, vol. 29, Apr. 2003, pp. 795-802.

Holzer, Mike P. et al., "Corneal flap complications in refractive surgery—Part 2: Postoperative treatments of diffuse lamellar keratitis in an experimental animal model", *J Cataract Refract Surg*, vol. 29, Apr. 2003, pp. 803-807.

Horwitz, Joseph, "α-Crystallin can function as a molecular chaperone", *Proc. Natl. Acad. Sci. USA*, vol. 89. Nov. 1992, pp. 10449-10453.

Huber, G. et al., "Room-temperature 2-pm HO:YAG and 3-pm ER:YAG Lasers", *Journal de Physique*, undated but prior to Jul. 2009, 3 pgs.

Hunter, David, "First, Gather the Data", *New England Journal of Medicine*, vol. 354, No. 4, Jan. 26, 2006, pp. 329-331.

Johannesson, Mattias, "Active Range Imaging 2", PhD-Thesis: SIMD architectures for Range and Radar Imaging, *Linkoping Studies in Science and Technology*, Dissertations No. 399, 2005, pp. 1-34.

Juhasz, Tibor, Ph.D. et al., "Dynamics of Shock Waves and Cavitation Bubbles Generated by Picosecond Laser Pulses in Corneal Tissue and Water", *Lasers in Surgery and Medicine*, vol. 15, 1994, pp. 91-98.

Kasthurirangan, Sanjeev et al., "Amplitude dependent accommodative dynamics in humans", *Vision Research*, vol. 43, 2003, pp. 2945-2956.

Kasthurirangan, Sanjeev, "Influence of Amplitude and Starting Point on Accommodative Dynamics in Humans", *IOVS*, vol. 46, No. 9, Sep. 2005, pp. 3463-3472.

Kaufman, Paul L., M.D., "Accommodation and Presbyopia: Neuromuscular and Biophysical Aspects", *Adler's Physiology of the Eye*, date unknown but prior to Jul. 2009, pp. 391-411.

König, Karsten et al., "Are Femtosecond Lasers Safe for Ophthalmic Applications?", *Fraunhofer Institute of Biomedical Technologies*, undated but prior to Jul. 2009, pp. 1-16.

König, Karsten et al., "Cornea surgery with nanojoule femtosecond laser pulses", *Proc. of SPIE*, vol. 5688, 2005, pp. 288-293.

König, Karsten et al., "First in vivo animal studies on intraocular nanosurgery and multiphoton tomography with low-energy 80 MHz near infrared femtosecond laser pulses", *Proc. of SPIE*, vol. 5314, 2004, pp. 262-269.

Koopmans, Steven a. et al., "Polymer Refilling of Presbyopic Human Lenses in Vitro Restores the Ability to Undergo Accommodative Changes", *IOVS*, vol. 44, No. 1, Jan. 2003, pp. 250-257.

Koretz, Jane F. et al., "Accommodation and Presbyopia in the Human Eye—Changes in the Anterior Segment and Crystalline Lens With Focus", *IOVS*, vol. 38, No. 3, Mar. 1997, pp. 569-578.

Koretz, Jane F. et al., "Scheimpflug and high-resolution magnetic resonance imaging of the anterior segment: a comparative study", *J. Opt. Soc. Am. A*, vol. 21, No. 3, Mar. 2004, pp. 346-354.

Krag, Susanne et al., "Biomechanical Characteristics of the Human Anterior Lens Capsule in Relation to Age", *Investigative Ophthalmology & Visual Science*, vol. 38, No. 2, Feb. 1997, pp. 357-362.

Krauss, Joel et al., "Laser Interactions With the Cornea", *Survey of Ophthalmology* A183, vol. 31, No. 1, Jul./Aug. 1986, pp. 37-53.

Kronemyer, Bob, "Accommodating IOL? Impossible, Recent Study Seems to Say". *Ocular Surgery News*, http://www.slackmc.com, Sep. 15, 1996, 2 pgs.

Krueger, Ronald R. et al., "First safety study of femtosecond laser photodisruption in animal lenses: Tissue morphology and cataractogenesis", *J Cataract Refract Surg*, vol. 31, Dec. 2005, pp. 2386-2394.

Krueger, Ronald R., M.D., et al., "Nonmechanical Microkeratomes Using Laser and Water Jet Technology", Publisher unknown, date unknown but prior to Jul. 2009, pp. 1-33.

Kuizenga, Dirk J., "FM-Laser Operatiob of the Nd:YAG Laser", *IEEE Journal of Quantum Electronics*, vol. 6, No. 11, 1970, pp. 673-677.

Kurapkienė, S. et al., "The relationship of ultrasonic and mechanical properties of human nuclear cataract. A pilot study", *Ultragarsas*, vol. 54, No. 1, 2005, pp. 39-43.

Kurtz, Ron et al., "Femtosecond Laser Corneal Refractive Surgery", *Proc. of SPIE*, vol. 3591, 1999, pp. 209-219.

Kurtz, Ron et al., "Ophthalmic Applications of Femtosecond Lasers", *Proc. f SPIE*, vol. 3616, 1999, pp. 51-65.

Kurtz, Ron M. et al., "Optimal Laser Parameters for Intrastromal Corneal Surgery", *Proc. of SPIE*, vol. 3255, 1998, pp. 56-66.

Kuszak, J. R. et al., "A Quantitative Analysis of Sutural Contributions to Variability in Back Vertex Distance and Transmittance in Rabbit Lenses as a Function of Development, Growth, and Age", *Optometry and Vision Science*, vol. 79, No. 3, Mar. 2002, pp. 193-204.

Kuszak, J. R. et al., "Biochemistry of the Crystalline Lens; Anatomy of Aged and Senile Cataractous Lenses", 1994, pp. 564-575.

Kuszak, J. R. et al., "Electron Microscope Observations of the Crystalline Lens", *Microscopy Research and Technique*, vol. 33, 1996, pp. 441-479.

Kuszak, J. et al., "Gap Junctions of Chick Lens Fiber Cells", *Exp. Eye Res.*, vol. 27, 1978, pp. 495-498.

Kuszak, J. R. et al., "Lens Optical Quality is a Direct Function of Lens Sutural Architecture", *Investigative Ophthalmology & Visual Science*, vol. 32, No. 7, Jun. 1991, pp. 2119-2129.

Kuszak, J. R. et al., "Quantitative Analysis of Animal Model Lens Anatomy: Accommodative Range is Related to Fiber Structure and Organization", undated but prior to Jul. 2009, 26 pgs.

Kuszak Jer R. et al., "The Structure of the Vertebrate Lens", Chapter 4, undated but prior to Jul. 2009, pp. 71-118.

Kuszak, J. et al., "The Surface Morphology of Embryonic and Adult Chick Lens-Fiber Cells", *The American Journal of Anatomy*, vol. 159, 1982, pp. 395-410.

Kuszak, J. R. et al., "The Use of an *Ex Vivo* Mechanical Stretching Apparatus to Examine Fiber Ultrastructure During Accommodation", undated but prior to Jul. 2009, 1 pg.

L'Esperance, Jr. "Ophthalmic Lasers Photocoagulation, Photoradiation and Surgery", $2^{nd}$ Edition, The C.V. Mosby Company, copyright 1983, pp. 529-538.

Lerman, Sidney, M.D., "Photosensitizing Drugs and Their Possible Role in Enhancing Ocular Toxicity", *Ophthalmology*, vol. 93, No. 3, Mar. 1986, pp. 304-318.

Lerman, Sidney, et al., "Photosensitization of the lens by 8-methoxypsoralen", *Invent. Ophthalmol. Visual Sci.*, vol. 16, No. 11, Nov. 1977, pp. 1065-1068.

Lerman, Sidney, et al., "Spectroscopic Evaluation and Classification of the Normal, Aging, and Cataractous Lens", *Ophthl. Res.*, vol. 8, 1976, pp. 335-353.

Loerscher, Hanspeter et al., "Noncontact Trephination of the Cornea Using a Pulsed Hydrogen Floride Laser", *American Journal of Ophthalmology*, vol. 104, Nov. 1987, pp. 471-475.

Loesel, Frieder H. et al., "Laser-Induced Optical Breakdown on Hard and Soft Tissues and Its Dependence on the Pulse Duration: Experiment and Model", *IEEE Journal of Quantum Electronics*, vol. 32, No. 10, Oct. 1996, pp. 1717-1722.

Lou, Marjorie F., et al., "Protein-Thiol Mixed Disulfides in Human Lens", published by Academic Press Limited, 1992, pp. 889-896.

Manns, Fabrice et al., "Radius of Curvature and Asphericity of the Anterior and Posterior Surface of Human Cadaver Crystalline Lenses", *Experimental Eye Research*, vol. 78, 2004, pp. 39-51.

Marion, II, John E. et al., "Medical Applications of Ultra-Short Pulse Lasers", *Proc. of SPIE*, vol. 3616, 1999, pp. 42-50.

Masters, B.R., "Three-dimensional Microscopic Tomographic Imaging of the Cataract in a Human Lens In Vivo", *Optics Express 332*, vol. 3, No. 9, Oct. 1998, pp. 332-338.

Mathias, R.T. et al., "Physiological Properties of the Normal Lens", *Physiological Reviews*, vol. 77, No. 1, Jan. 1997, pp. 21-50.
McDonald, Marguerita B., et al., "Central Photorefractive Keratectomy for Myopia, The Blind Eye Study", *Arch Ophthalmol*, vol. 108, Jun. 1990, pp. 799-808.
Mutti, Donald O., et al., "A Video Technique for Phakometry of the Human Crystalline Lens", *Investigative Ophthalmology, & Visual Science*, vol. 33, No. 5, Apr. 1992, pp. 1771-1781.
Myers, Raymond I. et al., "Feasibility of Using Lasers to Retard Cataract Development in the Ocular Lens by Restoring Lens Movement"; undated but prior to Jul. 2009, pp. 1-22.
Myers, Raymond I. et al., "Novel Approaches to Correction of Presbyopia With Laser Modification of the Crystalline Lens", *Journal of Refractive Surgery*, vol. 14, Mar./Apr. 1998, pp. 136-139.
Chinese Office Action for related application No. CN 200780009762.6, dated Mar. 2, 2011, 10 pgs.
Chinese Office Action for related application No. CN 200780009762.6, dated Sep. 9, 2010, 9 pgs.
International Search Report and Written Opinion for related application No. PCT/US2011/023159, dated Mar. 16, 2011, 6 pgs.
International Search Report and Written Opinion for related application No. PCT/US2011/023117, dated Mar. 25, 2011, 10 pgs.
International Search Report and Written Opinion for related application No. PCT/US2011/22859, dated Apr. 4, 2011, 7 pgs.
International Search Report and Written Opinion for related application No. PCT/US2010/041324, dated Sep. 23, 2010, 11 pgs.
International Search Report and Written Opinion for related application No. PCT/US2010/041286, dated Sep. 14, 2010, 8 pgs.
International Search Report and Written Opinion for related application No. PCT/US2010/042582, dated Sep. 20, 2010, 10 pgs.
International Search Report and Written Opinion for related application No. PCT/US2010/043255, dated Sep. 16, 2010, 10 pgs.
International Search Report and Written Opinion for related application No. PCT/US2010/043117, dated Sep. 10, 2010, 14 pgs.
Author unknown, "Statement of the Use of Animals in Opthalmic and Visual Research", The Association for Research in Vision and Opthalmology, Obtained from the Internet at: http"//www.arvo.org/aboutavro as of Nov. 18, 2010, 3 pgs.
Brian, G. et al., "Cataract Blindness—Challenges for the 21$^{st}$ Century", *Bulletin of the World Health Organization*, vol. 79, No. 3, 2001, pp. 249-256.
Eisner, Georg, "Eye Surgery—An Introduction to operative technique", Springer-Verlag, Berlin, 1980, pp. 14-19.
Garner, LF et al., "Changes in Equivalent and Gradient Refractive Index of the Crystalline Lens with Accommodation", *Optom, Vis. Sci.*, vol. 74, No. 2, Feb. 1997, pp. 114-119.
Garner, LF et al., "Changes in Ocular Dimensions and Refraction with Accommodation", *Ophthal. Physiol. Opt.*, vol. 17, No. 1, 1997, pp. 12-17.
Glasser, A. et al., "Biometric, optical and physical changes in the isolated human crystalline end with age in relation to presbyopia", *Vision Research*, vol. 39, 1999, pp. 1991-2015.
Glasser, A. et al., "On the potential causes of presbyopia", *Vision Research*, vol. 39, 1999, pp. 1267-1272.
Hanson, S.R.A. et al., "The major in vivo modifications of the human water-insoluble lens crystallins are disulfide bonds, deamidation, methionine oxidation and backbone cleavage", *Exp. Eye Res.*, vol. 71, 2000, pp. 195-207.
Juhasz, T. et al., "Time resolved observations of shock waves and cavitatin bubbles generated by femtosecond laser pulses in corneal tissue and water", *Lasers in Surgery and Med*, vol. 19, 1996, pp. 23-31.
Krueger, R.R., "Surfs Up—Catch a wave with a waterjet", *Jrn. Ref. Surg.*, vol. 14, No. 3, May/Jun. 1998, pp. 280-281.
Kuszak, JR et al., "The interrelationship of lens anatomy and optical quality II Primate Lenses", *Exp. Eye Res.*, vol. 59, 1994, pp. 521-535.
Lubatschowski, Holger, "Surgical Laser System for the Treatment of Presbyopia", 7$^{th}$ *Biotech in Europe Investor Forum*, Switzerland, Oct. 2-3, 2007, 9 pgs.
McBrien, N. A et al., "Experimental Myopia in a Diumal Mammal (*Sciurus carolinesis*) with No Accommodative Ability", *J. Physiol.*, vol. 469, 1993, pp. 427-441.

McCourt, M. E et al., Refractive State, Depth of Focus, and Accommodation of the Eye of the California ground squirrel (*Spermophiliu beecheyi*), Vision Res, vol. 24, No. 10, 1984, pp. 1261-1266.
Prokofeva, G. L et al., "Effects of Low-Intensity Infrared Laser Irradiation on the Eye, (An Experimental Study)", *Vestn. Oftalmol.*, vol. 112, No. 1, Jan.-Mar. 1996, pp. 31-32, with English Abstract, 5 pgs.
Sliney, D. H et al., "Medical Lasers and Their Safe Use", *Springer Verlag*, New York, 1993, pp. 42-50.
Vogel, Alfred et al., "Intraocular Photodisruption With Picosecond and Nanosecond laser Pulses: Tissue Effects in Cornea, Lens and Retina", *Investigative Ophthalmology & Visual Science*, Jun. 1994, No. 7, vol. 35, pp. 3032-3044.
Hammer, Daniel et al., "Shielding Properties of Laser-Induced Breakdown in Water for Pulse Durations From 5 ns to 125 fs", *Applied Optics*, 1997, vol. 36, No. 22, pp. 5630-5640.
International Search Report and Written Opinion for related application No. PCT/US2011/56279,dated Feb. 1, 2012, 9 pgs.
International Search Report and Written Opinion for related application No. PCT/US2012/030247,dated Jul. 9, 2012, 6 pgs.
International Search Report and Written Opinion for related application No. PCT/US2012/030059,dated Jul. 13, 2012, 12 pgs.
International Search Report and Written Opinion for related application No. PCT/US2012/030259,dated Jul. 13, 2012, 11 pgs.
Unpublished U.S. Appl. No. 13/427,130, filed Mar. 22, 2012 (34 pgs).
Unpublished U.S. Appl. No. 13/427,149, filed Mar. 22, 2012 (29 pgs).
Unpublished U.S. Appl. No. 13/427,319, filed Mar. 22, 2012 (32 pgs).
Unpublished U.S. Appl. No. 13/435,103, filed Mar. 30, 2012 (72 pgs).
U.S. Appl. No. 11/337,127, filed Jan. 20, 2006, Frey et al.
U.S. Appl. No. 11/414,819, filed May 1, 2006, Frey et al.
U.S. Appl. No. 12/217,285, filed Jul. 2, 2008, Frey et al.
U.S. Appl. No. 12/217,295, filed Jul. 2, 2008, Frey et al.
U.S. Appl. No. 12/509,021, filed Jul. 24, 2009, Frey et al.
U.S. Appl. No. 12/509,211, filed Jul. 24, 2009, Frey et al.
U.S. Appl. No. 12/509,412, filed Jul. 24, 2009, Frey et al.
U.S. Appl. No. 12/685,850, filed Jan. 12, 2010, Myers et al.
U.S. Appl. No. 12/831,845, filed Jul. 7, 2010, Naranjo-Tackman et al.
U.S. Appl. No. 12/831,859, filed Jul. 7, 2010, Naranjo-Tackman et al.
U.S. Appl. No. 12/840,818, filed Jul. 21, 2010, Porter et al.
U.S. Appl. No. 12/842,870, filed Jul. 23, 2010, Frey et al.
U.S. Appl. No. 29/377,018, filed Oct. 15, 2010, Bott et al.
U.S. Appl. No. 29/377,054, filed Oct. 15, 2010, Bott et al.
U.S. Appl. No. 13/016,593, filed Jan. 28, 2011, Frey et al.
U.S. Appl. No. 13/017,499, filed Jan. 31, 2011, Frey et al.
U.S. Appl. No. 13/017,702, filed Jan. 31, 2011, Frey et al.
U.S. Appl. No. 13/243,406, filed Sep. 23, 2011, Myers et al.
U.S. Appl. No. 13/273,653, filed Oct. 14, 2011, Frey et al.
U.S. Appl. No. 13/427,130, filed Mar. 22, 2012, Frey.
U.S. Appl. No. 13/427,149, filed Mar. 22, 2012, Frey et al.
U.S. Appl. No. 13/427,319, filed Mar. 22, 2012, Grey et al.
U.S. Appl. No. 13/435,103, filed Mar. 30, 2012, Curatu et al.
U.S. Appl. No. 13/681,004, filed Nov. 19, 2012, Frey et al.
FDA PMA P030002 titled "crystalens™ Model AT-45 Accomodating Posterior Chamber Intraocular Lens (IOL)", dated Nov. 14, 2003, 16 pgs.
FDA PMA P040020 titled "AcrySof®ResSTOR® Apodized Diffractive Optic Posterior Chamber Intraocular Lenses, Models MA60d3 and SA60D3", dated Mar. 21, 2005, 29 pgs.
Unpublished U.S. Appl. No. 13/681,004, filed Nov. 19, 2012 (57 pgs).
Bliss, E. S., "Pulse Duration Dependence of laser Damage Mechanisms", *Opto-Electronics*, vol. 3, 1971, pp. 99-108.
Chaker, M. et al., "Interaction of a 1 psec laser pulse with solid matter", *Phys. Fluids B 3*, vol. 1, Jan. 1991, pp. 167-175, plus cover page.
Chien, C. Y. et al., "Production of a high-density and high-temperature plasma with an intense high-contrast subpicosecond laser", *Optics Letters*, vol. 18, No. 18, Sep. 15, 1993, pp. 1535-1537.

Corkum, P. B. et al., "Thermal Response of Metals to Ultrashort-Pulse Laser Excitation", *Physical Review Letters*, vol. 61, No. 25, Dec. 19, 1988, pp. 2886-2889.

Du, D. et al., "Laser-induced breakdown by impact ionization in SiO2 with pulse widths from 7 ns to 150 fs", *Appl. Phys. Lett.*, vol. 64, No. 23, Jun. 6, 1994, pp. 3071-3073.

Klem, D. E. et al., "The Interaction of Intense Femtosecond Laser Pulses with Solid Targets", paper prepared under the auspices of the U.S. Dept. of Energy for the Short Wavelength V: Physics with Intense Laser Pulses Second Topical Meeting on Mar. 29-31, published Dece,ber 30, 1992, 1993, 6 pgs.

Liu, X. et al., "Competition between Ponderomotive and Thermal Forces in Short-Scale-Length Laser Plasmas", *Physical Review Letters*, vol. 69, No. 13, Sep. 28, 1992, pp. 1935-1938.

Müller, F. et al., "A Comparative Study of Deposition of Thin Films by Laser Induced PVD with Femtosecond and Nanosecond Laser Pulses", *SPIE*, vol. 1858, 1993, pp. 464-474.

Sauteret, C. et al., "Laser designers eye petawatt power",*Laser Focus World*, Oct. 1990, pp. 85-92 with cover page.

Soileau, M. J. et al., "Temporal Dependence of laser-Induced Breakdown in NaCl and $SiO_2$", prepared for Dept. of Physics, North Texas State University, publication date unknown, 19 pgs.

Stuart, B. C. et al., "Laser-Induced Damage in Dielectrics with Nanosecond to Subpicosecond Pulses", *Physical Review Letters*, vol. 74, No. 12, Mar. 20, 1995, pp. 2248-2251.

Wilks, S. C. et al., "Absorption of ultra-Intense Laser Pulses", *Physical Review Letters*, vol. 69, No. 9, Aug. 31, 1992, pp. 1383-1386.

* cited by examiner

LIQUID FILLED INDEX MATCHING DEVICE FOR OPHTHALMIC LASER PROCEDURES

This application claims the benefit of priority of provisional application Ser. No. 61/083,849 filed Jul. 25, 2008, the disclosure of which is incorporated herein by reference. The present invention relates to an apparatus for use in laser surgery on the eye and in particular during laser lens surgery. Thus, the present invention provides for a fluid filled patient interface device that follows the curvature of the patient's eye and reduces changes in the index of refraction between the docking station and the eye.

BACKGROUND OF THE INVENTION

In performing laser surgery on the eye, and in particular in performing laser surgery on the lens of the eye, such as for the purpose of performing a laser assisted capsulotomy, an interface device is needed that touches the anterior surface of the eye and docks with the laser device that is being used to perform the surgery. Such laser devices and systems are disclosed, for example in published applications US 2007/173794 A1, US 2007/173795 A1, US2007/185475 A1, WO 2007/084694 A2, WO 2007/084627 A2, the disclosures of which are incorporated herein by reference.

A particular problem that may occur with such interface devices arises because the laser beam must pass through the interface device which has a different index of refraction than the components of the eye that the laser beam must also pass through to reach the lens. This difference in the index of refraction creates difficulties in accurately placing the laser beam at a particular point in the lens of the eye or at particular points in other structures within the eye. Previously, this problem has been addressed by the use of complex mathematical algorithms that attempted to compensate for the difference in the index of refraction. Moreover, this problem is even further increased when the surfaces of the interface device through which the laser beam must travel are not flat.

SUMMARY

It is desirable to develop an interface device that reduces or eliminates these and other undesirable features of such devices. In particular it is desirable to have an interface device that has the same index of refraction as the cornea. In this way the refractive power and effects of the cornea are eliminated without the need to applanate the eye and the detrimental effects of applanation can be eliminated.

The present invention, among other things, solves this need by providing an index matching device comprising: curved patient interface lens; a sidewall; a glass plate; a leg; and, a laser device docking member; wherein the side wall, glass plate and curved patient interface lens form a fluid reservoir.

In a further embodiment, the present invention provides an index matching device comprising: a laser device docking ring; a plurality of legs each having a first and a second end; the first end of each leg being affixed to the laser docking ring; an annular side wall having a first and a second end; the first end of the annular side wall being affixed to the second end of the legs; a glass plate attached to the side wall adjacent to the first end of the side wall; a curved patient interface lens attached to the side wall adjacent the second end of the side wall; the side wall having a filling port; the glass plate, curved patient interface, and side wall forming a fluid reservoir; and the fluid reservoir containing an index matching fluid.

There is yet further provided an index matching device comprising: a fluid reservoir; the reservoir having a shape that in part follows the curvature of the eye; and the reservoir containing a fluid having an index of refraction that matches the index of refraction of a cornea, wherein the index matching device eliminates the refractive p power of the cornea.

DESCRIPTION OF THE DRAWINGS AND THE PREFERRED EMBODIMENTS

The present invention provides for a laser patient interface device that is fluid filled, with a fluid that matches the index of refraction of the anterior chamber of the eye and thus greatly reduces any difference in the index of refraction between the eye and the interface device.

Figure 1:
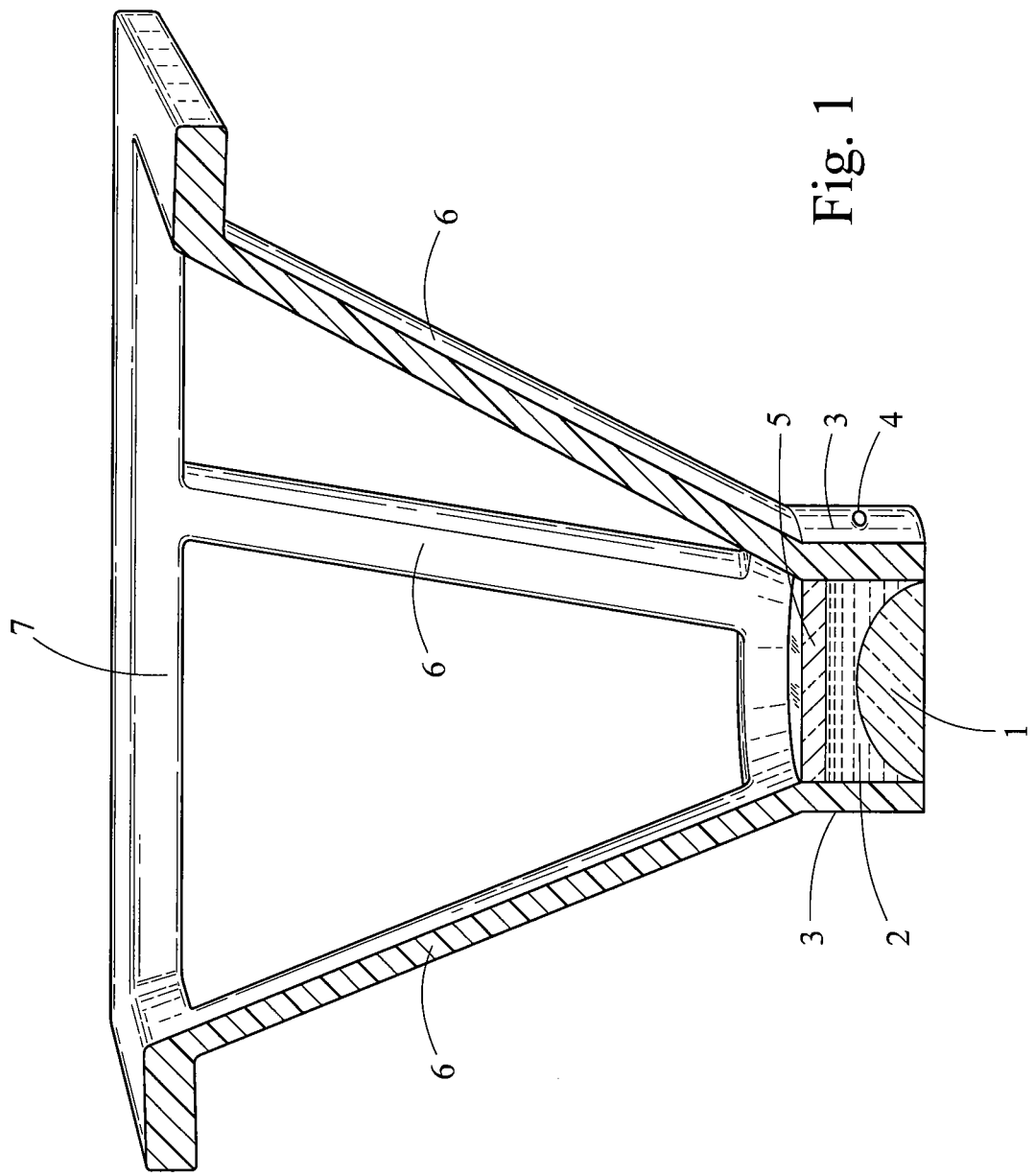
FIG. 1 is a sectional diagram of an index matching device of the present invention.

In general, as shown in FIG. 1, there is provided an index matching device for use in the performance of ophthalmic laser surgery. Thus, there is provided by way of example a curved patient interface lens 1, a fluid reservoir 2, a side wall for the reservoir 3, a filling port 4 for the reservoir 2, and a glass plate 5. The side wall 3 is circular and the side wall 3, glass plate 5 and curved patient interface lens 1 are connected together in a manner that is fluid tight to form the fluid reservoir 2.

The reservoir 2 can be filled with a fluid having a known index of refraction and thus the index of refraction can be set to match and/or approximate the index of refraction of the lens. Thus, the reservoir is preferably filled with a saline solution that has been degassed. Moreover, although the preferred embodiment of the present invention is to match or as closely as possible approximate the index of refractions of the device to that of the eye, in other applications having a known and predetermined difference may be advantageous. Thus, the reservoir may be filled with a particular index matching fluid having a predetermined and known index of refraction, such as those that are obtainable from NYE and CARGILLE LABS.

The curved patient interface lens 1 is shaped to follow the curvature and shape of the anterior surface of the eye. Thus, different shapes and sizes of curved patient interface lens 1 may be employed depending upon the patient. The curved patient interface lens 1 may be a commercially available hard contact lens, or it may be made of similar materials to those used to make such contact lens. The curved lens has a thickness of about that of a contact lens and has a diameter of about 12 to 12.5 mm.

Figure 3:
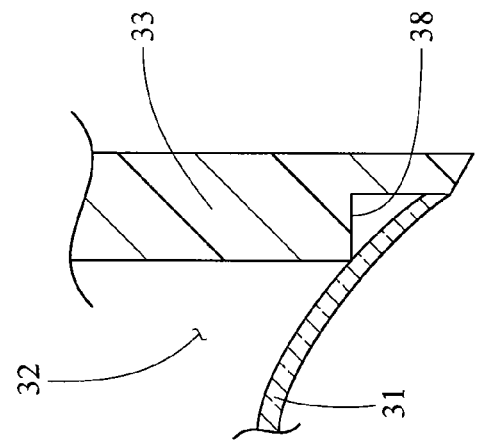
FIG. 3 is a detailed cross section diagram of an index matching device of the present invention showing the side wall ledge and curved patient interface lens.

The side wall may be made of plastic or metal. The curved patient interface lens 1 may be attached to the side wall by glue, pressure fit, snap fit or other connecting means known to the art, provided that the connection is fluid tight so as to prevent fluid from leaking out of the reservoir. A detail of the manner in which the curved patient interface lens adjoins the side wall is provided in FIG. 3. Thus, in this figure there is provided a curved patient interface lens 31, a reservoir 32, side wall 33, which has a ledge 38 upon which the lens 32 rests. Returning to FIG. 1, there is further shown a filling port 4. The port may be of any type known to the art that will allow for easy filling of the reservoir and which does not leak after being filled. The port may be sealed with an epoxy glue or other sealing means. Alternatively, a small piece of metal tape or other similar material may be used over the top of the port on the outside of the side wall 3 to seal the port after filling. If an aqueous solution is used as the index matching fluid, it is desirable to degass the solution prior to filling to prevent generation of bubbles in the fluid reservoir.

The glass plate 5 is as thin as practicable and may be about 0.5 mm to 2 mm in thickness. The glass plate may have a diameter of about 11 mm. The glass plate may be affixed to the device by glue, pressure fit or other techniques known to the art that would provide a fluid tight seal.

Figure 2:
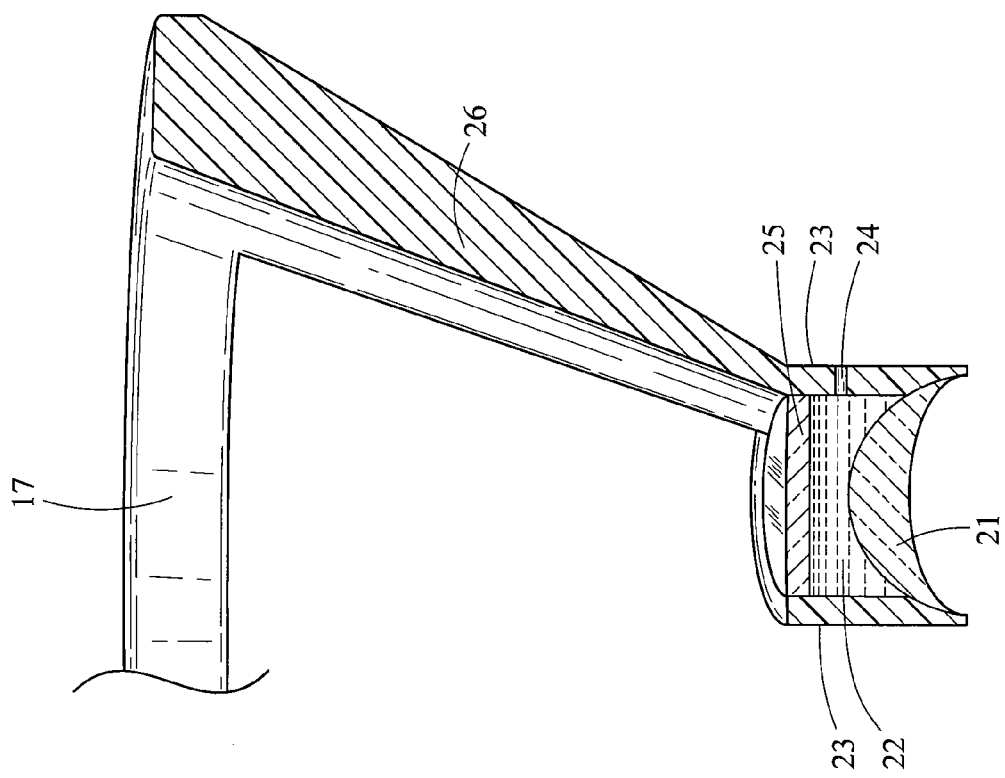
FIG. 2 is a cross section diagram of an index matching device of the present invention.

The side wall 3 is connected to legs 6 which are connected to ring 7. The ring 7 is the portion of the device that is attached, or docked with, the laser surgery device. Thus, the shape of this ring is dependent upon and should match with the docking features of the laser surgery device. A different embodiment of the legs and ring are shown in FIG. 2. In that figure there is only a single leg. Thus, there is provided a curved patient interface lens 21, a reservoir 22, a side wall 23, a filling port 24, a glass plate 25, a single leg 26 and a docking member 17. The docking member 17 does not necessarily have to be a ring or circular.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. An index matching device comprising:
   a curved patient interface lens having a shape that in part follows a curvature of an eye to which the index matching device is coupled;
   a sidewall comprising a top surface and a bottom surface;
   a planar glass plate that extends along a plane, wherein the curved patient interface lens is attached to the top surface and the planar glass plate is attached to the bottom surface;
   wherein the side wall extends, from the planar glass plate to the curved patient interface lens, perpendicular to the plane, and wherein the curved patient interface lens, the side wall and the planar glass place define a fluid tight volume of a fluid reservoir;
   a leg; and,
   a laser device docking member, wherein a first end of the leg is attached to the side wall and a second end of the leg is attached to the laser device docking member.

2. The index matching device of claim 1, wherein the fluid reservoir is filled with saline.

3. The index matching device of claim 2, wherein the fluid reservoir is filled with a fluid having a predetermined index of refraction.

4. The index matching device of claim 1, wherein the index matching device eliminates a power of a cornea of the eye.

5. The index matching device of claim 1, wherein the side wall is an annular side wall.

6. The index matching device of claim 1, wherein the side wall comprises a filling port that can be in fluid communication with the fluid tight volume of the fluid reservoir.

7. An index matching device comprising:
   a laser device docking ring;
   a plurality of legs each having a first end and a second end;
   the first end of each of the plurality of legs being affixed to the laser device docking ring;
   a side wall having a first end and a second end;
   the first end of the side wall being affixed to the second end of each of the plurality of legs;
   a planar glass plate attached to the side wall adjacent to the first end of the side wall, wherein the planar glass plate extends along a plane and the side wall extends perpendicular to the plane;
   a curved patient interface lens attached to the side wall adjacent the second end of the side wall, wherein the side wall extends, from the planar glass plate to the curved patient interface lens, perpendicular to the plane, and wherein the curved patient interface lens defining a shape that in part follows a curvature of an eye to which the index matching device is coupled;
   the glass plate, the curved patient interface, and the side wall forming a fluid tight volume of a fluid reservoir; and
   the fluid tight volume of the fluid reservoir containing a fluid.

8. The index matching device of claim 7, wherein an index of refraction of the fluid matches an index of refraction of a cornea of the eye, whereby a power of the cornea is eliminated.

9. The index matching device of claim 7, wherein an index of refraction of the fluid has a predetermined index of refraction that is different than an index of refraction of a cornea of the eye.

10. The index matching device of claim 7, wherein the side wall is an annular side wall.

11. The index matching device of claim 7, wherein the side wall comprises a filling port that can be in fluid communication with the fluid tight volume of the fluid reservoir.

12. An index matching device comprising:
   a fluid reservoir comprising:
      a curved patient interface lens defining a shape that in part follows a curvature of an eye to which the index matching device is coupled;
      a sidewall comprising a top surface and a bottom surface;
      a planar glass plate that extends along a plane, wherein the curved patient interface lens is attached to the top surface and the planar glass plate is attached to the bottom surface; and
      wherein the side wall extends, from the planar glass plate to the curved patient interface lens, perpendicular to the plane, and wherein the curved patient interface lens, the sidewall and the planar glass plate define a fluid tight volume of the fluid reservoir; and
   the fluid tight volume of the reservoir containing a fluid having an index of refraction that matches an index of refraction of a cornea of the eye.

13. The index matching device of claim 12, wherein the fluid is saline.

14. The index matching device of claim 12, wherein the index matching device eliminates a power of the cornea.

15. The index matching device of claim 12, wherein the side wall is an annular side wall.

16. The index matching device of claim 12, wherein the side wall comprises a filling port that can be in fluid communication with the fluid tight volume of the fluid reservoir.

* * * * *

UNITED STATES PATENT AND TRADEMARK OFFICE
CERTIFICATE OF CORRECTION

PATENT NO. : 8,500,723 B2  
APPLICATION NO. : 12/509021  
DATED : August 6, 2013  
INVENTOR(S) : Frey et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 913 days.

Signed and Sealed this  
Twenty-fourth Day of February, 2015

Michelle K. Lee  
*Deputy Director of the United States Patent and Trademark Office*